United States Patent
Dykhuizen et al.

(10) Patent No.: US 10,976,320 B2
(45) Date of Patent: Apr. 13, 2021

(54) METHODS FOR IDENTIFYING AND TREATING CANCER PATIENTS

(71) Applicants: Emily Carla Dykhuizen, West Lafayette, IN (US); Diana Clare Hargreaves, San Mateo, CA (US); Cigall Kadoch, Tiburon, CA (US); Gerald R. Crabtree, Woodside, CA (US)

(72) Inventors: Emily Carla Dykhuizen, West Lafayette, IN (US); Diana Clare Hargreaves, San Mateo, CA (US); Cigall Kadoch, Tiburon, CA (US); Gerald R. Crabtree, Woodside, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 14/284,324

(22) Filed: May 21, 2014

(65) Prior Publication Data

US 2015/0185221 A1 Jul. 2, 2015

Related U.S. Application Data

(60) Provisional application No. 61/826,001, filed on May 21, 2013.

(51) Int. Cl.
| | |
|---|---|
| *G01N 33/574* | (2006.01) |
| *A61K 31/352* | (2006.01) |
| *A61K 31/704* | (2006.01) |
| *A61K 31/496* | (2006.01) |
| *C12Q 1/6886* | (2018.01) |
| *A61K 31/475* | (2006.01) |
| *A61K 31/473* | (2006.01) |
| *A61K 31/05* | (2006.01) |
| *A61K 31/136* | (2006.01) |
| *A61K 31/353* | (2006.01) |
| *A61K 31/7048* | (2006.01) |

(52) U.S. Cl.
CPC ....... *G01N 33/57496* (2013.01); *A61K 31/05* (2013.01); *A61K 31/136* (2013.01); *A61K 31/352* (2013.01); *A61K 31/353* (2013.01); *A61K 31/473* (2013.01); *A61K 31/475* (2013.01); *A61K 31/496* (2013.01); *A61K 31/704* (2013.01); *A61K 31/7048* (2013.01); *C12Q 1/6886* (2013.01); *C12Q 2600/106* (2013.01); *C12Q 2600/158* (2013.01); *G01N 2333/914* (2013.01); *G01N 2800/52* (2013.01)

(58) Field of Classification Search
CPC .. A61K 31/352; A61K 31/496; A61K 31/704; A61K 31/00; C12Q 1/6886; C12Q 2600/158; C12Q 2600/106; G01N 2333/914; G01N 33/57496; G01N 2800/52

See application file for complete search history.

(56) References Cited

U.S. PATENT DOCUMENTS

| | | | | |
|---|---|---|---|---|
| 2006/0121449 | A1* | 6/2006 | Tjotta | G01N 33/5005 435/5 |
| 2013/0156795 | A1* | 6/2013 | Iavarone | C12Q 1/6886 424/174.1 |

OTHER PUBLICATIONS

Kadoch et al. (2013) Nature Genetics 45: 592-601.*
Dykhuizen et al. (2013) Nature 497 (7451): 624-627.*
Spyropoulou et al. (2013) Neuromolecular Medicine 15(1): 1-24. Published online Nov. 1, 2012 (Year: 2013).*
Neely et al. (2002) Biochimica et Biophysica Acta 1603(1): 19-29. (Year: 2002).*
Katagiri, Atsuko, et al. "Loss of ARID1A expression is related to shorter progression-free survival and chemoresistance in ovarian clear cell carcinoma." Modern Pathology 25.2 (2012): 282-288. (Year: 2012).*
Opipari, Anthony W., et al. "Resveratrol-induced autophagocytosis in ovarian cancer cells." Cancer research 64.2 (2004): 696-703. (Year: 2004).*
Anglesio, Michael S., et al. "Type-specific cell line models for type-specific ovarian cancer research." PloS one 8.9 (2013). (Year: 2013).*
Hargreaves et al. Cell Res. 21:396-420 (2011).
Kadoch et al. Nature Genet. 45:592-601 (2013).
You et al. Cancer Cell 22:9-20 (2012).
Clapier et al. Annu. Rev. Biochem. 78:273-304 (2009).
Ho et al. Nature Cell Biol. 13:903-913 (2011).
Wilson et al. Cancer Cell 18:316-328 (2010).
Parsons et al. Science 331:435-439 (2011).
Pugh et al. Nature 488:106-110 (2012).
Jones et al. Nature 488:100-105 (2012).
Robinson et al. Nature 488:43-48 (2012).
Love et al. Nature Genet. 44:1321-1325 (2012).
Richter et al. Nature Genet. 44:1316-1320 (2012).

(Continued)

*Primary Examiner* — Robert J Yamasaki
(74) *Attorney, Agent, or Firm* — David A. Roise; VLP Law Group LLP

(57) ABSTRACT

Methods for identifying and treating cancer patients likely to respond to topoisomerase inhibitors or likely to fail to respond to topoisomerase inhibitors are provided. The methods take advantage of the newly discovered role of BAF complexes in decatenation of DNA by topoisomerase IIa. Cancer cells are frequently at least partly defective in BAF complex activity. Such cells are targeted for therapy using certain topoisomerase IIa inhibitors according to the disclosed methods of treatment. Therapy of such cells using other topoisomerase inhibitors should be avoided.

11 Claims, 23 Drawing Sheets

(56) References Cited

OTHER PUBLICATIONS

Barbieri et al. Nature Genet. 44:685-689 (2012).
Versteege et al. Nature 394:203-206 (1998).
Kadoch et al. Cell 153:71-85 (2013).
Sigauke et al. Mod. Pathol. 19:717-725 (2006).
Haberler et al. Am. J. Surg. Pathol. 30:1462-1468 (2006).
Lichner et al. Am. J. Pathol. 182:1163-1170 (2013).
Wiegand et al. J. Pathol. 224:328-333 (2011).
Carpenter et al. Mol. Biol. Cell 15:5700-5711 (2004).
Lou et al. J. Nature Struct. Mol. Biol. 12:589-593 (2005).
Dawlaty et al. Cell 133:103-115 (2008).
Ramamoorthy et al. Nucleic Acids Res. 40:1621-1635 (2012).
Ho et al. Proc. Natl Acad. Sci. USA 106:5181-5186 (2009).
Johnson et al. Nucleic Acids Res. 37:e98 (2009).
Downes et al. Nature 372:467-470 (1994).
Luo et al. Nature Cell Biol. 11:204-210 (2009).
Sakaguchi et al. J. Cell Sci. 117:1047-1054 (2004).
Khavari et al. Nature 366:170-174 (1993).
Kool et al. Acta Neuropathol. 123:473-484 (2012).
Northcott et al. Nature Rev. Cancer 12:818-834 (2012).
Stros et al. Nucleic Acids Res. 35:5001-5013 (2007).
Sano et al. PLoS ONE 3:e4103 (2008).
Capranico et al. Nucleic Acids Res. 18:4553-4559 (1990).
Sperling et al. Proc. Natl Acad. Sci. USA 108:12693-12698 (2011).
Bourgo et al. Mol. Biol. Cell 20:3192-3199 (2009).
Janssen et al. Science 333:1895-1898 (2011).
Bultman et al. Genes Dev. 19:2849-2861 (2005).
Barski et al. Cell 129:823-837 (2007).
Langmead et al. Genome Biol. 10:R25 (2009).
Zhang et al. Genome Biol. 9:R137 (2008).
Quinlan et al. Bioinformatics 26:841-842 (2010).
Kent et al. Genome Res. 12:996-1006 (2002).
Meyer et al. Nucleic Acids Res. 41:D64-D69 (2012).
Shankavaram et al. BMC Genomics (2009) 10:277; doi:10.1186/1471-2164-10-277.
Dykhuizen et al. Nature (2013) 497:624-627.

\* cited by examiner

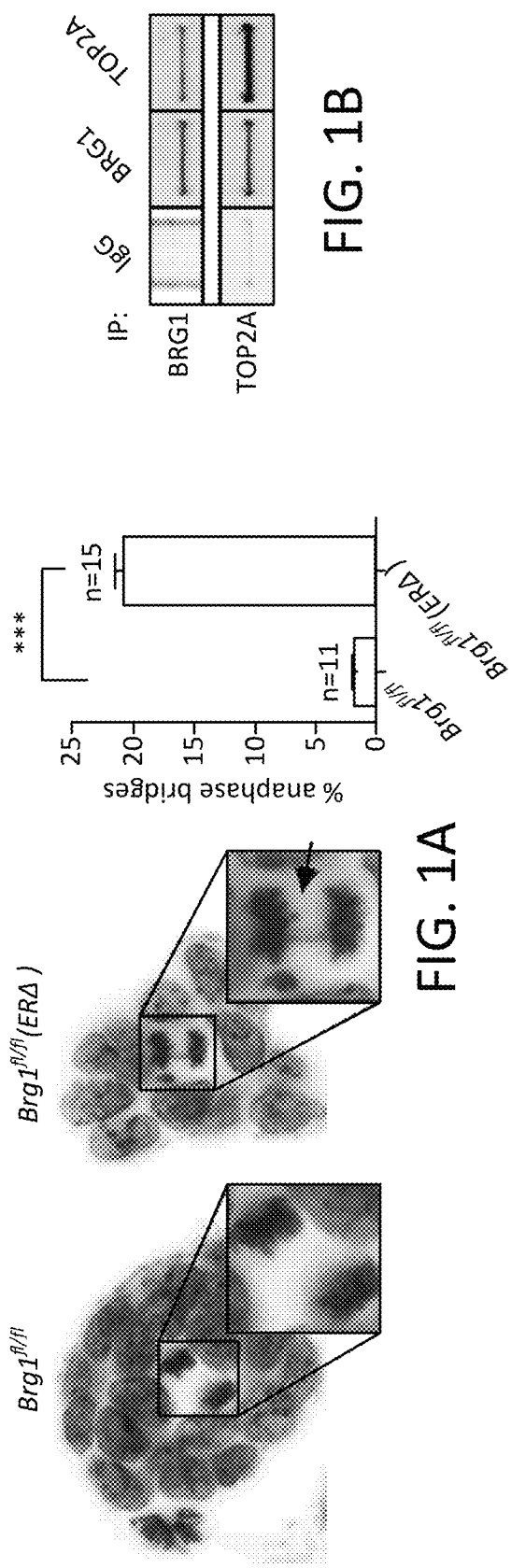
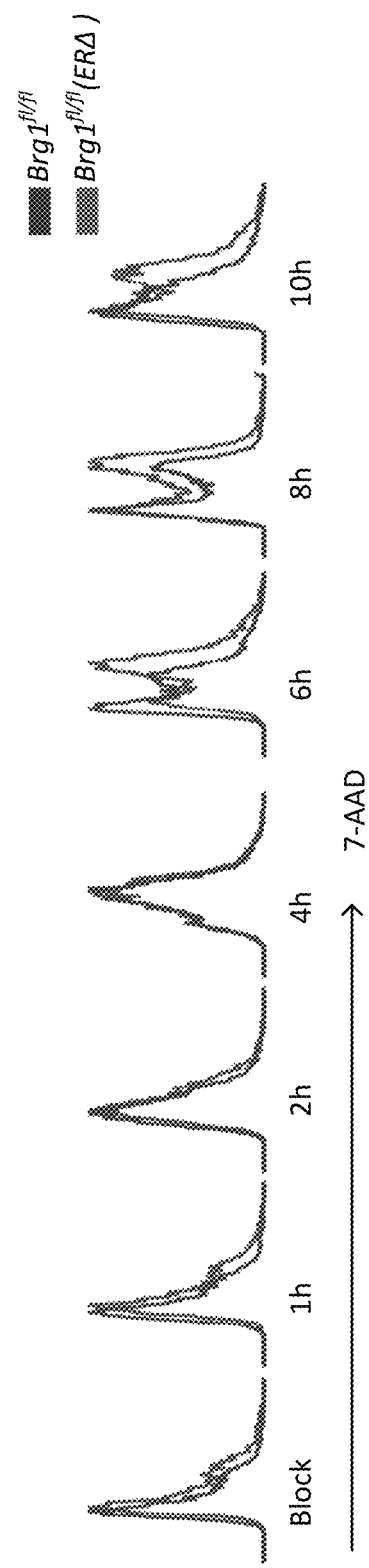
FIG. 1A
FIG. 1B
FIG. 1C

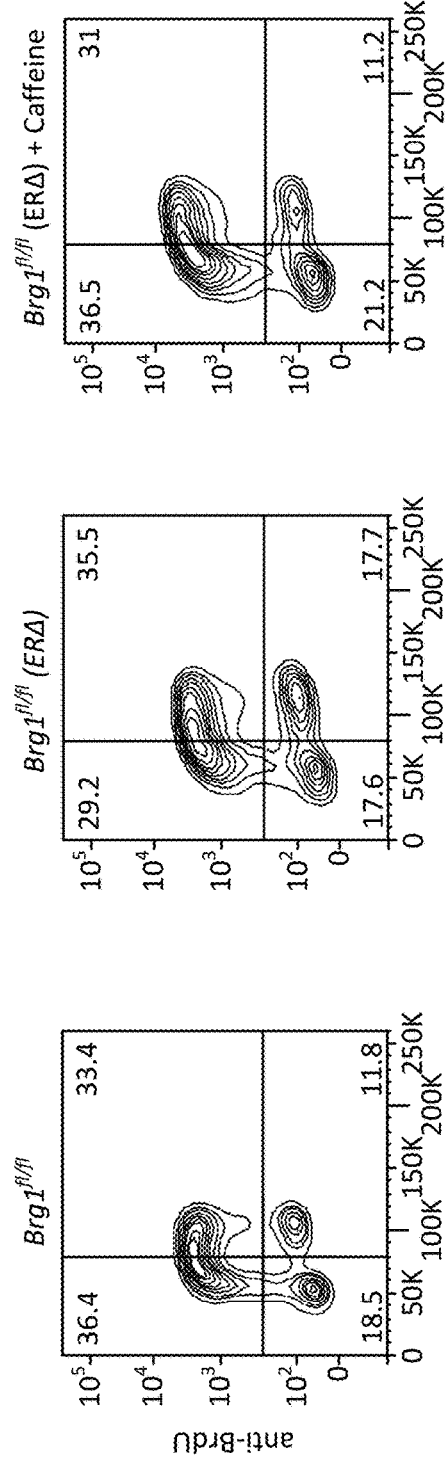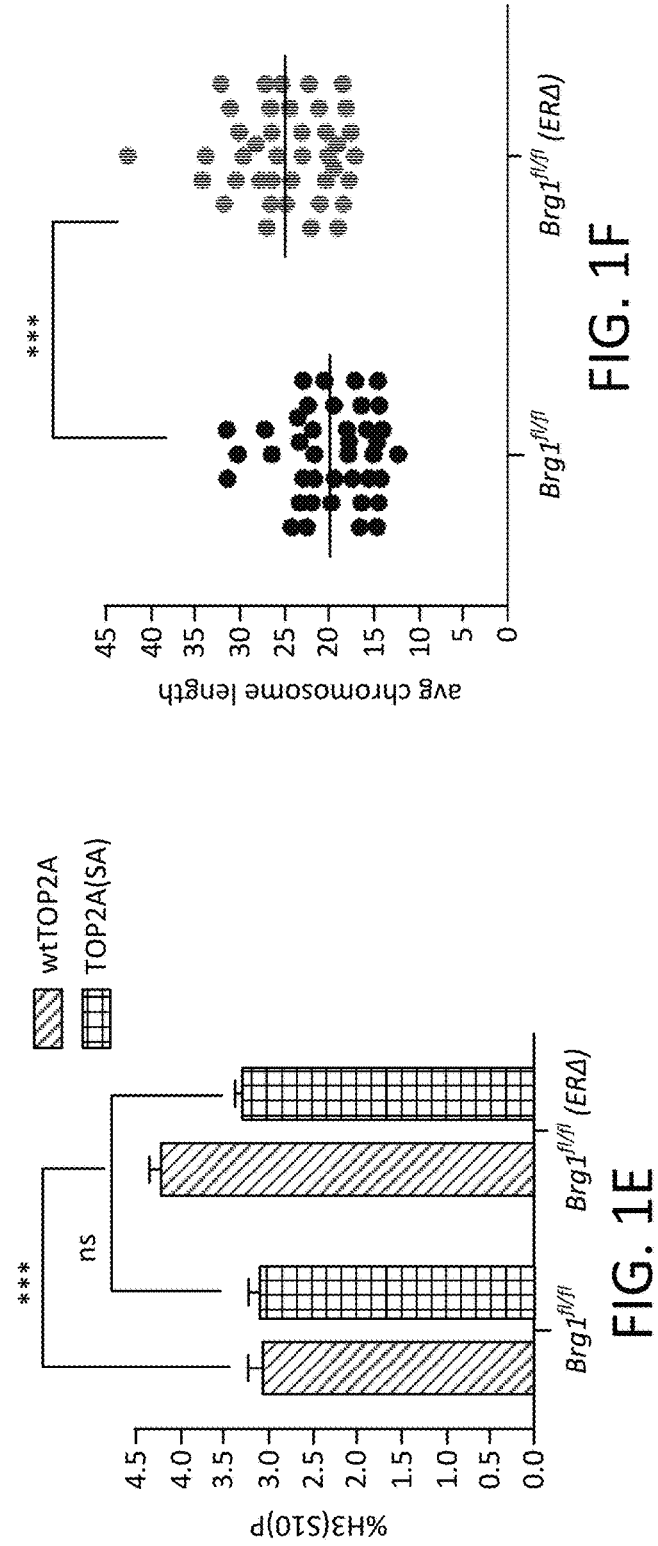
FIG. 1D FIG. 1E FIG. 1F

| Cell Type | AT/ Total Cells | % AT Cells |
|---|---|---|
| vector | 6/57 | 10.5% |
| wtBRG1 | 3/64 | 4.7% |
| BRG1(GD) | 26/89 | 29.2%* |
| BRG1(TM) | 32/107 | 29.9%* |
| vector + Tax | 7/51 | 13.7% |
| wtBRG1 + Tax | 7/64 | 10.9% |
| BRG1(GD) + Tax | 18/54 | 33.3%* |
| BRG1(TM) + Tax | 31/78 | 39.7%* |

| Tissue Type | Bridges (Total Anaphases) | % Anaphase Bridges |
|---|---|---|
| MEF | 11 (979) | 1.1% |
| E12.5 Brain | 6 (308) | 1.9% |
| control MB | 1 (57) | 1.8% |
| S1 | 2 (28) | 7.1% |
| S2 | 11 (48) | 22.9% |
| S3 | 1 (22) | 4.5% |
| S4 | 13 (86) | 15.1% |
| S5 | 1 (6) | 16.7% |

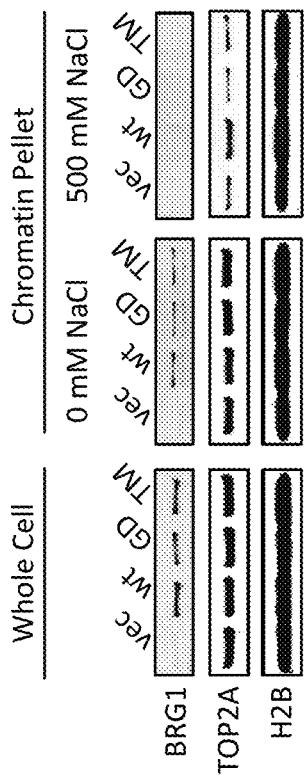
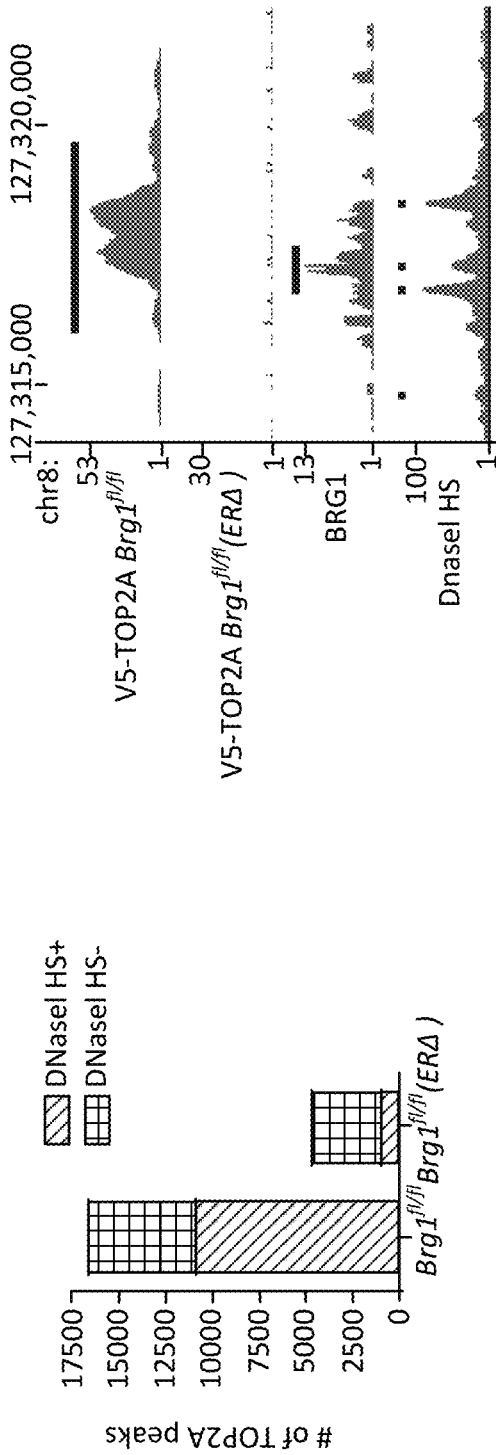
FIG. 3A
FIG. 3B
FIG. 3C

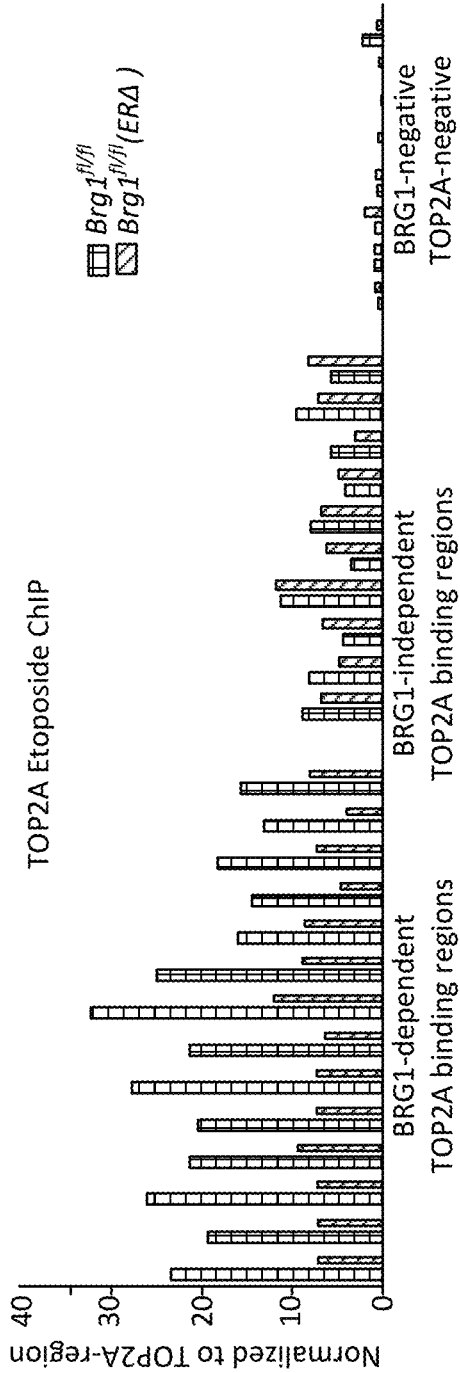
FIG. 3D
FIG. 3E
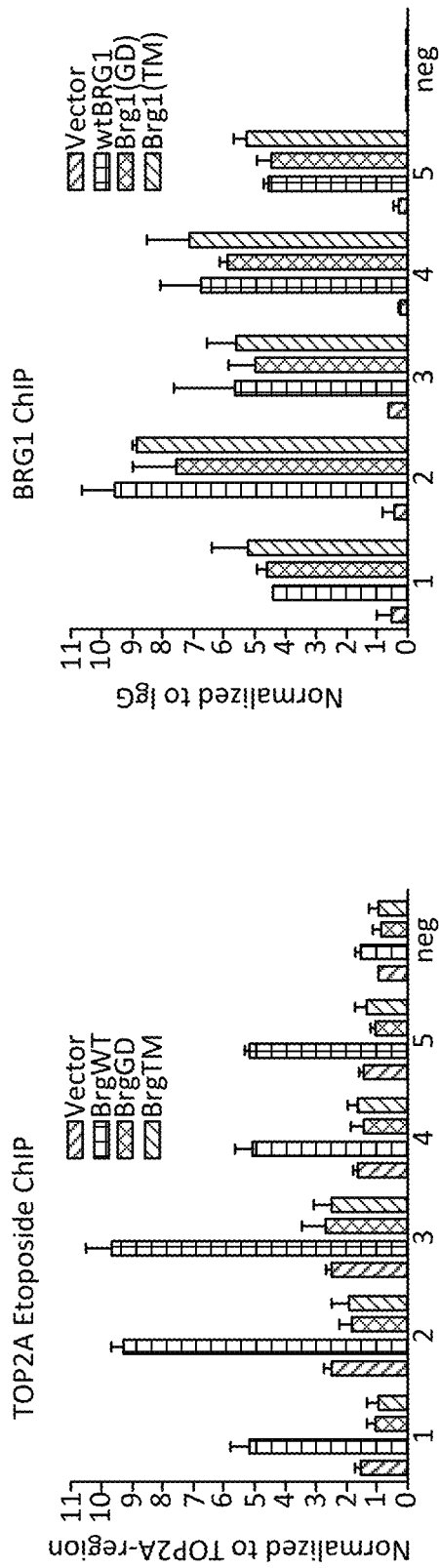
FIG. 3F

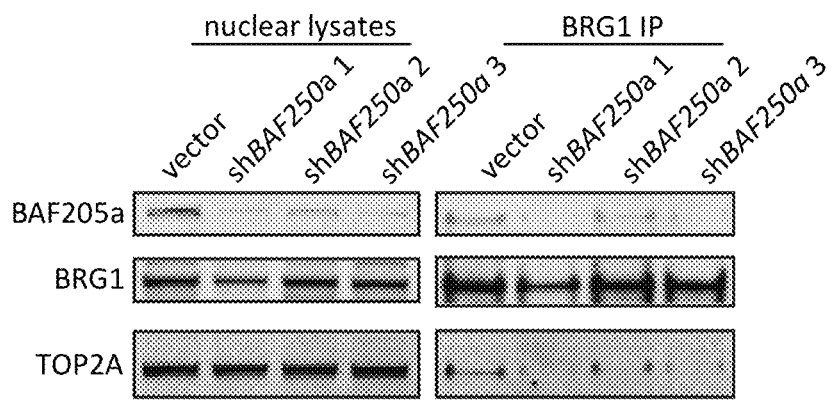
FIG. 4C
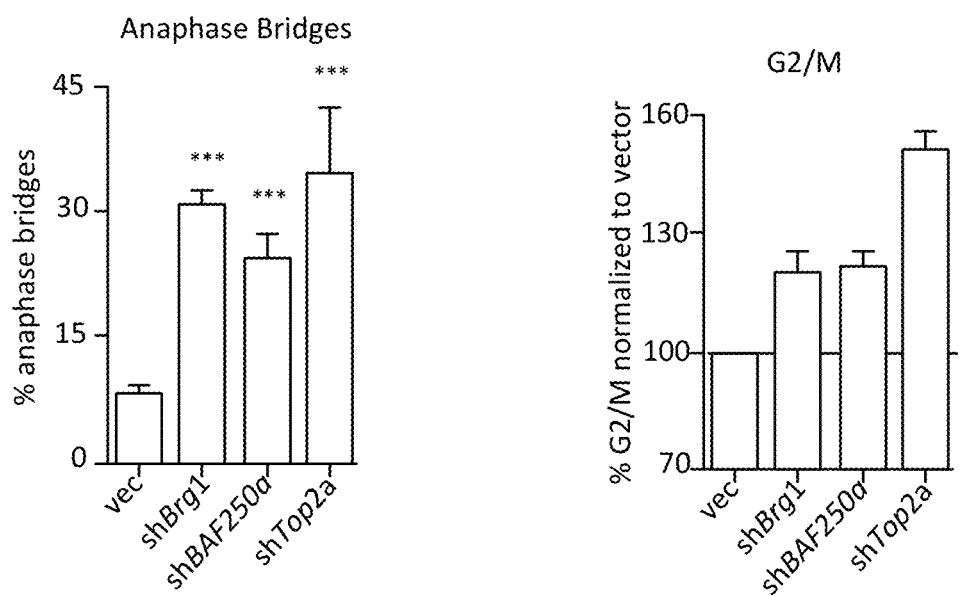
FIG. 4D
FIG. 4E

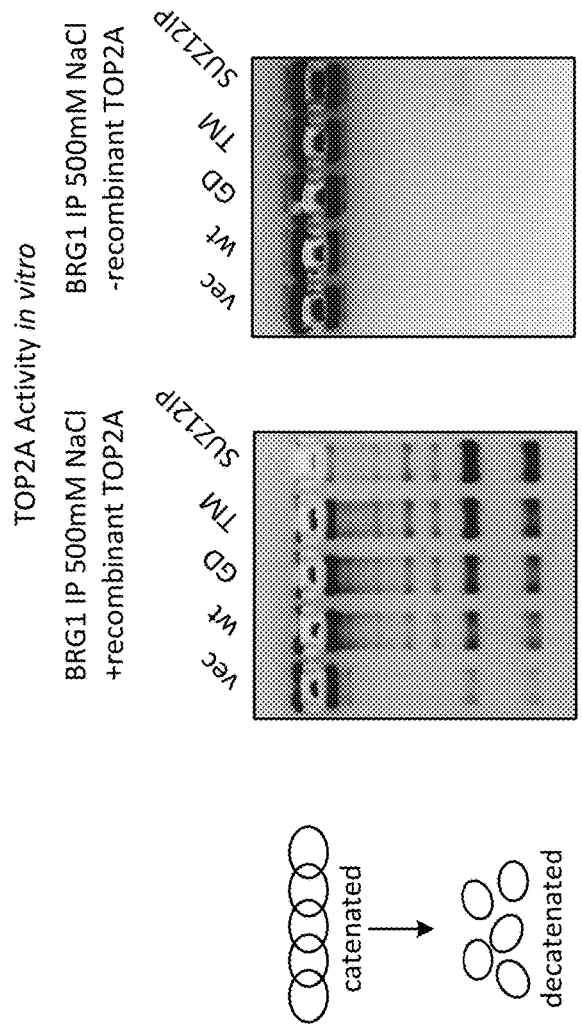
FIG. 9A
FIG. 9B
FIG. 9C

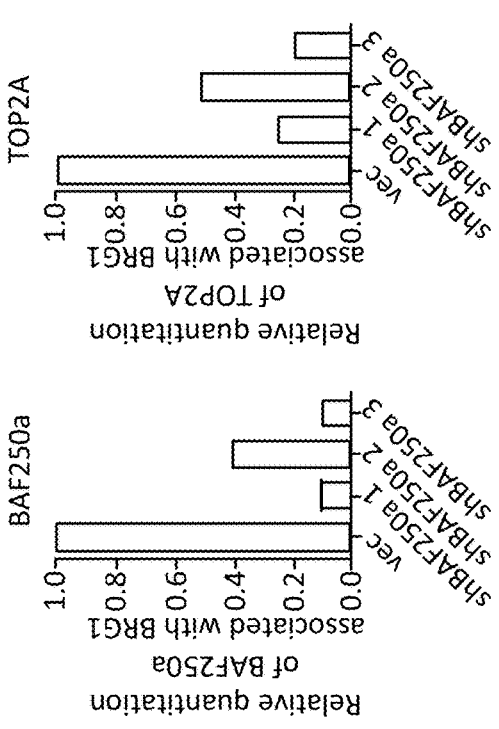
FIG. 10A
FIG. 10B
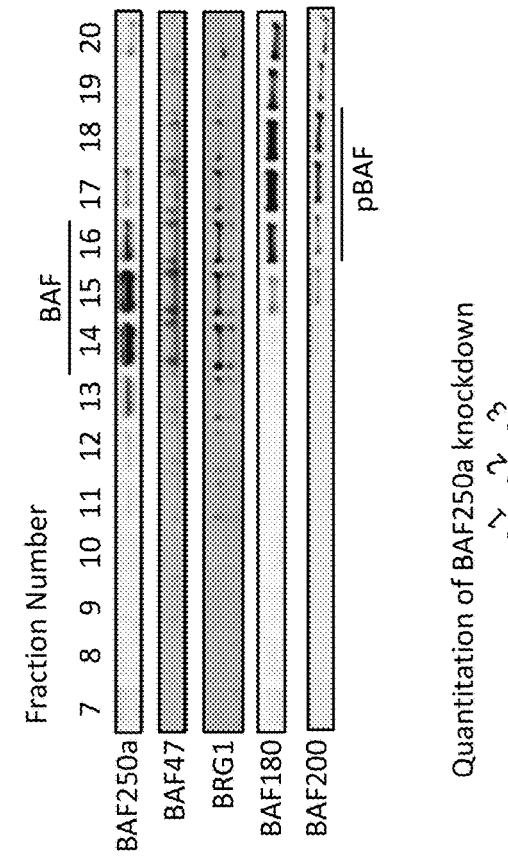
FIG. 10C
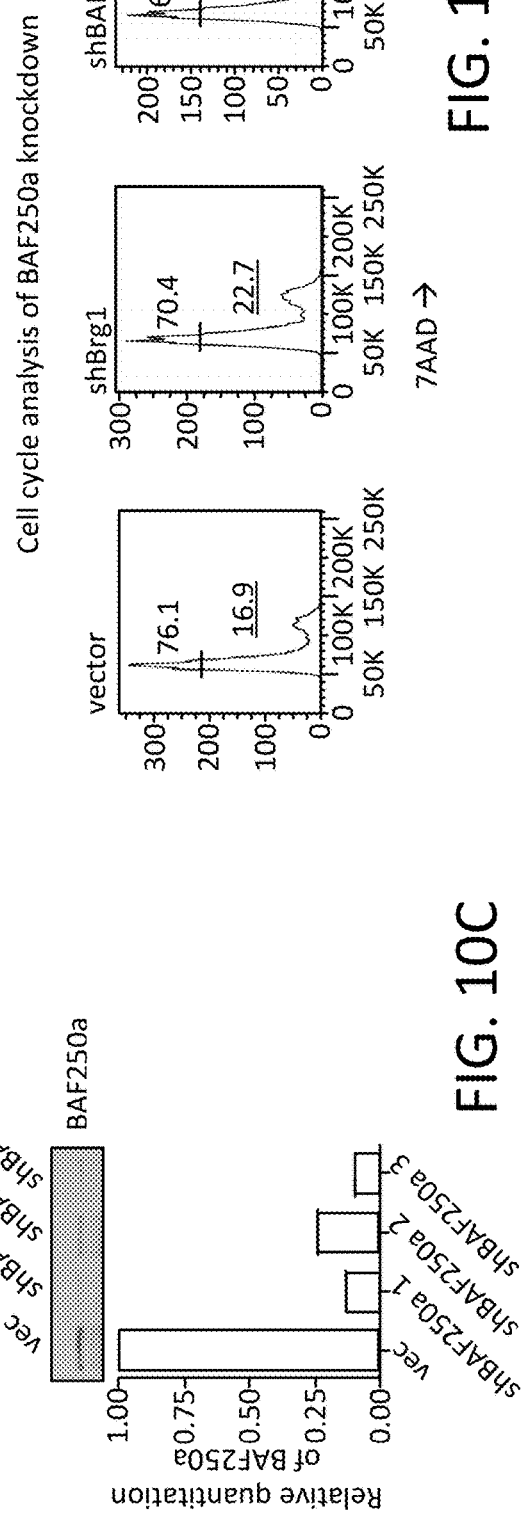
FIG. 10D

METHODS FOR IDENTIFYING AND TREATING CANCER PATIENTS

CROSS-REFERENCE TO RELATED APPLICATION

This application claims the benefit of U.S. Provisional Application No. 61/826,001, filed on May 21, 2013, the disclosure of which is incorporated herein by reference in its entirety.

STATEMENT OF GOVERNMENTAL SUPPORT

This invention was made with Government support under contracts CA163915 and NS046789 awarded by the National Institutes of Health. The government has certain rights in this invention.

BACKGROUND OF THE INVENTION

The targeting of specific therapeutics to specific diseases based on the genetic and/or biochemical features of the particular disease is increasingly important in maximizing the effectiveness of treatments and minimizing side effects. For example, identifying cancer patients likely to respond to a given treatment can improve outcomes and decrease costs. Equally important is the identification of patients unlikely to respond to the treatment, as those patients can avoid the unpleasant and potentially toxic side effects of a drug treatment regimen that will not provide them any therapeutic effect. Identification of non-responsive patients likewise saves the cost of the treatment, an important consideration as the costs of highly specialized and sophisticated new drugs are often quite high.

An early example of the usefulness of genetic testing in guiding treatment and predicting outcome can be found in the treatment of breast cancer with Herceptin. Herceptin is a monoclonal antibody that interacts with the HER2 receptor and can be effective in the treatment of certain breast cancers. Vogel et al. *J. Clin. Oncol.* 20:719-726 (2002); Slamon et al. *N. Engl. J. Med.* 344:783-792 (2001); Marty et al. *J. Clin. Oncol.* 23:4265-4274 (2005). The effectiveness is limited to breast cancers in which the HER2 gene is amplified, however, and indeed if the breast cancer doesn't overexpress HER2, Herceptin has no beneficial effect and may cause cardiac disruption or other side effects. Treatment with Herceptin is therefore only recommended where the cancer cells have been found to overexpress HER2. In a second example, the biomarker PGP has been prospectively used to indicate the potential resistance to etoposide, doxorubicin, or epirubicin. Baekelandt et al. *Anticancer Res* 20(2B): 1061-1067 (2000); Holzmayer et al. *J Natl Cancer Inst* 84(19): 1486-1491 (1992). The use of genetic, biochemical, and other types of testing to guide human therapy is becoming increasingly common and important as the mechanisms underlying disease become better known and understood.

Topoisomerases are enzymes that are targeted by a variety of widely used cancer drugs but have not previously been known to be selectively targetable by a genetic or biochemical means. Topoisomerases act on DNA during the cell cycle, catalyzing and guiding the unknotting or unkinking of DNA by creating transient breaks in the DNA.

Topoisomerases are divided into two types, depending on the number of strands cut per catalytic cycle. Topoisomerases of type I cut a single strand of the DNA double helix, allow relaxation, and then reanneal the cut strand. Topoisomerases of type II cut both stands of the DNA double helix, allow another unbroken DNA double helix to pass through the break, and then reanneal the cut strands. Type I and type II are each further subdivided depending on their mechanism and source. Several topoisomerase inhibitors bind to topoisomerases in the DNA bound conformation and prevent reannealing of cut strands, causing DNA double strand breaks and cell death.

Inhibitors of topoisomerases are widely used as antibiotics and anti-cancer drugs. Although topoisomerase inhibitors are in many cases effective chemotherapeutics, they can also be extremely toxic. Furthermore, they may lead to secondary neoplasms due to their DNA damaging properties.

There is thus a need for new and improved methods for identifying patients with cancers that are susceptible to treatment with topoisomerase inhibitors and for treating only those patients shown to have this susceptibility.

SUMMARY OF THE INVENTION

The present invention addresses these and other problems by providing novel methods relating to identifying and treating a cancer patient.

In one aspect, the methods comprise the steps of:
obtaining a tumor sample and a non-tumor sample from a cancer patient;
determining activities of at least one BAF subunit in the tumor sample and in the non-tumor sample; and
comparing the activities of the at least one BAF subunit in the tumor sample and in the non-tumor sample to determine the likelihood of effectiveness of treatment with a topoisomerase inhibitor.

In another aspect, the methods comprise the steps of:
obtaining a tumor sample and a non-tumor sample from a cancer patient;
determining activities of at least one BAF subunit in the tumor sample and in the non-tumor sample;
comparing the activities of the at least one BAF subunit in the tumor sample and in the non-tumor sample to determine the likelihood of effectiveness of treatment with a topoisomerase inhibitor; and
treating the patient with the topoisomerase inhibitor if the likelihood of effectiveness of treatment is increased or unchanged and not treating the patient with the topoisomerase inhibitor if the likelihood of effectiveness of treatment is decreased.

In yet another aspect, the methods comprise the steps of:
requesting an analysis of a tumor sample and a non-tumor sample from a cancer patient to determine activities of at least one BAF subunit in the tumor sample and in the non-tumor sample to determine the likelihood of effectiveness of treatment with a topoisomerase inhibitor; and
treating the patient with the topoisomerase inhibitor if the likelihood of effectiveness of treatment is increased or unchanged and not treating the patient with the topoisomerase inhibitor if the likelihood of effectiveness of treatment is decreased.

In some embodiments, the at least one BAF subunit is encoded by SMARCA4, SMARCA2, ARID1A, ARID1B, ARID2, PBRM1, BCL11A, BCL11B, BCL7A, BCL7B, BCL7C, SMARCB1, SMARCD1, SMARCD2, SMARCD3, SMARCC1, SMARCC2, PHF10, DPF1, DPF2, DPF3, ACTL6A, ACTL6B, BRD9, SS18, or SMARCE1.

In preferred embodiments, the at least one BAF subunit is encoded by SMARCA4, ARID1A, ARID1B, ARID2, PBRM1, BCL11A, BCL11B, BCL7A, or SMARCB1.

In some embodiments, the tumor sample is a colorectal cancer, a clear-cell ovarian cancer, a serous ovarian cancer, a pancreatic cancer, a gastric cancer, a bladder cancer, a hepatocellular cancer, a renal cancer, a squamous cell carcinoma, a breast cancer, a medulloblastoma, a glioma, a melanoma, a lung cancer, a prostate cancer, a sarcoma, a malignant rhabdoid tumor, or a hematologic malignancy.

In preferred embodiments, the tumor sample is a colorectal cancer, a clear-cell ovarian cancer, a pancreatic cancer, a gastric cancer, a bladder cancer, a hepatocellular cancer, a renal cancer, a breast cancer, a medulloblastoma, a lung cancer, a prostate cancer, a sarcoma, a malignant rhabdoid tumor, or a hematologic malignancy.

In some embodiments, the topoisomerase inhibitor is etoposide, teniposide, doxorubicin, daunorubicin, mitoxantrone, amsacrine, ellipticine, or epirubicin. In other embodiments, the topoisomerase inhibitor is aurintricarboxylic acid, HU-331, epigallocatechin gallate, genistein, quercetin, resveratrol, or ICRF-193. In preferred embodiments, the topoisomerase inhibitor is etoposide or doxorubicin.

According to some embodiments of the disclosure, the activities of the at least one BAF subunit in the tumor sample and in the non-tumor sample are determined by sequencing a portion of the gene encoding the at least one BAF subunit in the tumor sample and in the non-tumor sample. A mutation in the gene encoding the at least one BAF subunit in the tumor sample indicates a decreased activity of the at least one BAF subunit.

According to other embodiments, the activities of the at least one BAF subunit in the tumor sample and in the non-tumor sample are determined by measuring transcription of a gene encoding the at least one BAF subunit in the tumor sample and in the non-tumor sample. A decreased transcription of the gene encoding the at least one BAF subunit in the tumor sample indicates a decreased activity of the at least one BAF subunit.

According to still other embodiments, the activities of the at least one BAF subunit in the tumor sample and in the non-tumor sample are determined by measuring protein expression of the at least one BAF subunit in the tumor sample and in the non-tumor sample. A decreased protein expression of the at least one BAF subunit in the tumor sample indicates a decreased activity of the at least one BAF subunit.

In some embodiments, the activities of the at least one BAF subunit in the tumor sample and in the non-tumor sample are determined by measuring post-translational modifications of the at least one BAF subunit.

In still other embodiments, the activities of the at least one BAF subunit in the tumor sample and in the non-tumor sample are determined by measuring decatenation of DNA by topoisomerase IIa in the tumor sample and in the non-tumor sample, and a decreased decatenation of DNA by topoisomerase IIa in the tumor sample indicates a decreased activity of the at least one BAF subunit.

In specific embodiments, the activities of at least two BAF subunits in the tumor sample and in the non-tumor sample are determined, and a decreased activity of at least one BAF subunit in the tumor sample indicates an altered likelihood of effectiveness of treatment with a topoisomerase inhibitor.

In more specific embodiments, the activities of at least five BAF subunits in the tumor sample and in the non-tumor sample are determined, and a decreased activity of at least one BAF subunit in the tumor sample indicates an altered likelihood of effectiveness of treatment with a topoisomerase inhibitor.

In some embodiments, a decreased activity of the at least one BAF subunit in the tumor sample indicates an increased likelihood of effectiveness of treatment with a topoisomerase inhibitor. In other embodiments, a decreased activity of the at least one BAF subunit in the tumor sample indicates a decreased likelihood of effectiveness of treatment with a topoisomerase inhibitor. In still other embodiments, a decreased activity of the at least one BAF subunit in the tumor sample indicates an unchanged likelihood of effectiveness of treatment with a topoisomerase inhibitor.

BRIEF DESCRIPTION OF THE DRAWINGS

FIG. 1A-FIG. 1F. BRG1 associates with Topo2A and regulates its function. FIG. 1A, Anaphase bridges in $Brg1^{fl/fl}$ and $Brg1^{fl/fl}$(ERD) ESCs. Data represent number of slides from four independent experiments±s.e.m. FIG. 1B, Co-immunoprecipitation of BRG1 and Topo2A from nuclear lysates. FIG. 1C, DNA content in $Brg1^{fl/fl}$ and $Brg1^{fl/fl}$(ERD) ESCs after release from double thymidine block. FIG. 1D, Cell cycle analysis of $Brg1^{fl/fl}$ and $Brg1^{fl/fl}$(ERD) ESCs with or without caffeine, an ATM/ATR inhibitor. FIG. 1E, Data represent five independent histone H3 serine 10 phosphorylation (H3(S10)P cell cycle analyses±s.e.m. FIG. 1F, Data represent the mean of the average chromosome length per cell from 40 cells from metaphase spreads of $Brg1^{fl/fl}$ and $Brg1^{fl/fl}$(ERD) MEFs from two independent experiments.

FIG. 2A, Somatic mutations in BRG1 found in medulloblastoma. HAS=helicase and associated with SANT domain, BROMO=bromodomain, DEXD/H=DEAD/DEAH box helicase domain. FIG. 2B, The DNA-stimulated ATPase activity of BAF complexes from wtBRG1, BRG1(GD), BRG1(KR), BRG1(TM) and vector control-expressing $Brg1^{fl/fl}$(ERD) cells±s.e.m. FIG. 2C, Cell cycle analysis of $Brg1^{fl/fl}$ MEFs expressing wtBRG1, BRG1(GD), BRG1(TM), or vector, treated with ethanol (EtOH) or tamoxifen (Tax). FIG. 2D, Cells were prepared as in FIG. 2C and the mean frequency of anaphase bridges±s.e.m. from three independent experiments was measured. FIG. 2E, Cells were prepared as in FIG. 2C and collected for metaphase spreads. The number of cells with greater than 40 chromosomes (AT) was quantitated from >50 cells. Significance was calculated relative to vector control, ethanol-treated $Brg1^{fl/fl}$ cells where *P<0.05, P<0.01, *P<0.0001. FIG. 2F, Various tissues were sectioned and scored for the number of anaphase bridges of total anaphases.

FIG. 3A-FIG. 3F. BRG1 facilitates the binding of Topo2A to chromatin in vivo through ATPase-dependent chromatin-remodeling activity. FIG. 3A, Chromatin pellets isolated from nuclei of wtBRG1, BRG1(GD), BRG1(TM) and vector-expressing $Brg1^{fl/fl}$(ERD) ESCs lysed in ±500 mM NaCl. FIG. 3B, The number of DNase-I-hypersensitive Topo2A peaks of the total number of Topo2A peaks from Topo2A ChIP-seqs in $Brg1^{fl/fl}$ and $Brg1^{fl/fl}$(ERD) ESCs. FIG. 3C, Representative ChIP-seq tracks for Topo2A (in $Brg1^{fl/fl}$ and $Brg1^{fl/fl}$(ERD) ESCs), BRG1 and DNase I hypersensitivity (HS). FIG. 3D, Topo2A ChIP-qPCR confirmation from $Brg1^{fl/fl}$ and $Brg1^{fl/fl}$(ERD) ESCs. FIG. 3E, Topo2A ChIP-qPCR confirmation from wtBRG1, BRG1(GD), BRG1(TM) and vector control-expressing $Brg1^{fl/fl}$(ERD) ESCs. FIG. 3F, BRG1 ChIP-qPCRs from wtBRG1, BRG1(GD), BRG1(TM), and vector control-expressing $Brg1^{fl/fl}$(ERD) ESCs. FIG. 3E and FIG. 3F, Data represent means of triplicate experiments±s.e.m.

FIG. 4A-FIG. 4E. Topo2A associates with the BAF complex through BAF250a. FIG. 4A, Immunoprecipitates from ESC nuclear lysates. Quantitation of the precipitated Topo2A is shown. FIG. 4B, V5 was precipitated from HEK293T cells that had been transfected with Flag-Topo2A and either vector, V5-tagged full-length BAF250a (BAF250a FL) or V5-tagged BAF250a fragments. Lysates and anti-V5 precipitates were blotted for anti-V5, anti-Flag and anti-BRG1. FIG. 4C, BRG1 was immunoprecipitated from ESCs after BAF250a knockdown. FIG. 4D, MEFs with knockdown of Brg1, BAF250a or Top2a. Anaphase bridge frequency is calculated for seven experiments±s.e.m. Significance was calculated relative to vector control cells where *P<0.05, P<0.01 and *P<0.0001. FIG. 4E, Cell cycle analysis of MEFs from FIG. 4D. Data represent the mean of the percentage of G2/M cells normalized to vector control from four experiments±s.e.m.

FIG. 5A, ESC nuclei were lysed and treated +/− DNase I. BRG1 was IP'ed with an anti-BRG1 antibody (Santa Cruz) from untreated or treated lysates and assayed for its association with Topo2A. Nuclear lysates were run side-by-side to demonstrate that the association is independent of histones and DNA. FIG. 5B, To assay the efficiency of DNase I in the experiment in FIG. 5A, the untreated and DNase I-treated nuclear lysates were run on a 1% agarose gel and stained with EtBr. FIG. 5C, BRG1 was immunoprecipitated from HEK293T or MEF nuclear lysates with an anti-BRG1 antibody (Santa Cruz) and assayed for its association with Topo2A. FIG. 5D, Brg1$^{fl/fl}$ ESCs were infected with human RNAi-resistant wild-type Topo2A (wtTopo2A) or Topo2AS1524A (Topo2A(SA)) and shRNAs to mouse Topo2A. Cells were stained with anti-H3(S10)P and analyzed by flow cytometry 72 hours after treatment with or without tamoxifen. FIG. 5E, Metaphase spreads from Brg1$^{fl/fl}$ and Brg1$^{fl/fl}$(ERΔ) MEFs.

FIG. 6A, wild-type BRG1 (wt), BRG1(GD) (GD), BRG1(KR) (KR), or BRG1 (TM) (TM)-containing BAF complexes were immunoprecipitated from Brg1$^{fl/fl}$(ERΔ) ESCs with anti-Flag and analyzed for associated proteins by Western blot. FIG. 6B, The number of viable BRG1(GD), BRG1(KR), BRG1(TM), and vector-expressing Brg1$^{fl/fl}$(ERΔ) ESCs was measured and normalized to that of wtBRG1 Brg1$^{fl/fl}$(ERΔ) ESCs. FIG. 6C, Bar graphs displaying the percentage of cells in FIG. 2C with greater than 4N content from three experiments. Significance was calculated relative to vector control, ethanol treated Brg1$^{fl/fl}$ cells where *p<0.05, p<0.01, *p<0.0001. FIG. 6D, Representative images of anaphase bridges and normal anaphases from each of the BRG1 mutant medulloblastoma tumors quantitated in FIG. 2F.

FIG. 7A, Brg1$^{fl/fl}$ and Brg1$^{fl/fl}$(ERΔ) ESCs were lysed and Topo2A levels were assayed by western blot. FIG. 7B, Top2a transcript levels were assayed from Brg1$^{fl/fl}$ and Brg1$^{fl/fl}$(ERΔ) ESCs. FIG. 7C, Topo2A was immunoprecipitated with an anti-Topo2A antibody (Abcam) from Brg1$^{fl/fl}$ and Brg1$^{fl/fl}$(ERΔ) ESC nuclei and blotted for various post-translational modifications. FIG. 7D, Nuclear lysates from Brg1$^{fl/fl}$ and Brg1$^{fl/fl}$(ERΔ) ESCs were blotted for Topo2A to detect the higher molecular weight SUMO-modified form of Topo2A. FIG. 7E, BRG1 was immunoprecipitated with an anti-BRG1 antibody (Santa Cruz) from lysates prepared in either 150 mM or 500 mM NaCl and assayed for its association with Topo2A. The association between BRG1 and Topo2A is disrupted at 500 mM NaCl, making it possible to assay BAF and Topo2A independently. FIG. 7F, Topo2A was immunoprecipitated with an anti-Topo2A antibody (Abcam) from Brg1$^{fl/fl}$ and Brg1$^{fl/fl}$(ERΔ) ESCs in the presence of 500 mM NaCl to remove BRG1 (see FIG. 7E) and assayed for its ability to decatenate kinetoplast DNA (kDNA) in vitro at three different concentrations. The in vitro decatenation activity of three concentrations of IgG IP was assayed in parallel as a control. Unmanipulated kDNA starting material was run alongside the IPs for reference. Topo2A isolated from Brg1$^{fl/fl}$ or Brg1$^{fl/fl}$(ERΔ) ESCs has the same in vitro activity.

FIG. 8A, Brg1$^{fl/fl}$ and Brg1$^{fl/fl}$(ERΔ) MEFs were stained for Topo2A, centromeres, and DAPI. The overlay of Topo2A and centromeres, and all three is shown to demonstrate the relative localization of Topo2A to centromeres at four stages of the cell cycle. The colocalization of Topo2A with centromeres is similar in Brg1$^{fl/fl}$ and Brg1$^{fl/fl}$(ERΔ) MEFs. FIG. 8B, Brg1$^{fl/fl}$ and Brg1$^{fl/fl}$(ERΔ) MEFs were stained for Topo2A, γtubulin, and DAPI. The overlay of Topo2A and γtubulin, and all three is shown to demonstrate that the localization of Topo2A on chromosome arms is similar in Brg1$^{fl/fl}$ and Brg1$^{fl/fl}$(ERΔ) MEFs.

FIG. 9A-FIG. 9C. The in vitro decatenation activity of Topo2A is subject to non-specific regulation. FIG. 9A, Kinetoplast DNA was incubated with or without recombinant Topo2A (1 U or 0 U) and anti-BRG1 IPs from wtBRG1 (wt), BRG1(GD) (GD), BRG1(TM) (TM), or vector-expressing Brg1$^{fl/fl}$(ERΔ) ESCs precipitated in the presence of 500 mM NaCl to remove Topo2A (see FIG. 7E) or immunoprecipitated PRC2 (SUZ12). The decatenation activity of Topo2A is enhanced with the addition of any IP, despite the fact that the BRG1 mutants display decatenation defects in vivo and that PRC2 is not a known regulator of Topo2A, indicating that the decatenation activity of Topo2A may be enhanced by non-specific DNA-binding in this assay. FIG. 9B, Quantitation of 500 mM chromatin pellet in FIG. 3A. Nuclei from wtBRG1 (wt), BRG1(GD) (GD), BRG1(TM) (TM), or vector-expressing Brg1$^{fl/fl}$(ERΔ) ESCs were lysed in the presence of 500 mM NaCl. The insoluble chromatin pellet was western blotted for Topo2A and histone H2B. The blots were then quantitated and the value of the Topo2A signal over the H2B signal was calculated. FIG. 9C, Supernatant from the experiment in FIG. 3A was blotted for BRG1, Topo2A and histone H2B.

FIG. 10A-FIG. 10D. Anaphase bridge and cell cycle analysis in BAF250a deficient cells. FIG. 10A, Glycerol gradients were prepared from ESCs and fractions 7-20 were blotted for the indicated proteins. FIG. 10B, The amount of precipitated BAF250a and precipitated Topo2A was quantitated from Western blotting BRG1 immunoprecipitations in FIG. 4C. FIG. 10C, ESCs were infected with lentiviruses containing hairpins to BAF250a. Nuclear lysates were harvested and blotted for BAF250a. The relative quantitation of the western blot normalized to vector is shown below. FIG. 10D, 7AAD plots of the data from FIG. 4E of MEFs infected with lentiviruses containing hairpins to Brg1 and BAF250a.

FIG. 11A: treatment with etoposide; FIG. 11B: treatment with doxorubicin; FIG. 11C: treatment with ICRF-193.

DETAILED DESCRIPTION OF THE INVENTION

Figure 2A:
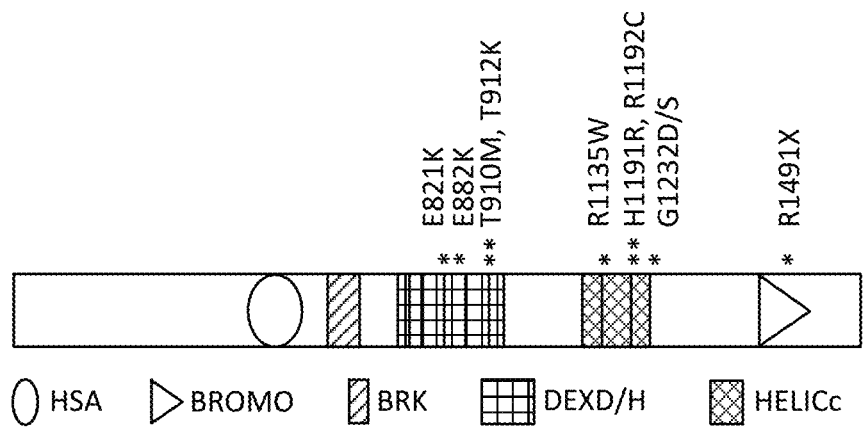
FIG. 2A-FIG. 2F. Expression of medulloblastoma-associated BRG1 mutants phenocopies Topo2A inhibition.

The genetic material of a cell (DNA) is compressed into the nucleus by intricate processes that must allow the DNA to be available to be replicated and selectively expressed. This task is accomplished by several mechanisms that include the assembly of DNA onto nucleosomes and then the selective modification of nucleosomes to allow further compaction of the DNA or to allow the DNA to be available (accessible) to the actions of proteins and processes that regulate the expression of genes encoded within the DNA sequences. The processes are thought to operate to regulate the chromatin state of DNA including DNA methylation, histone modification, and ATP-dependent chromatin regulation.

A chromatin regulatory complex necessary for the accessibility of DNA to regulatory mechanisms has been purified and partly characterized. See, e.g., Hargreaves and Crabtree *Cell Res.* 21:396-420 (2011). This complex, termed the BAF complex, is made up of 15 subunits encoded by 29 genes. Six of the genes are similar to those found in a yeast chromatin regulatory complex, SWI/SNF, and the name mSWI/SNF has therefore also been used to describe the complexes in higher cells. (The terms BAF and mSWI/SNF are used interchangeably throughout the instant disclosure.) The complexes are thought to control the mobility of nucleosomes on DNA and to regulate the phasing of nucleosomes by allowing transcription factors to bind to DNA.

Shortly after the complexes were purified and characterized, it was found that many cell lines had inactive, non-functional BAF complexes. Introduction of the wild-type subunits into the cell lines led to the proposal that the complexes were tumor suppressors. More recently, human genome sequencing studies have confirmed this impression. However the mechanism by which BAF complexes protect cells from cancer has not been clear, and various theories have been supported including direct regulation of cyclins, interaction with retinoblastoma, functions in DNA repair and transcriptional misregulation of cell cycle genes.

As described in the instant disclosure, the inventors have now determined that BAF complexes interact with topoisomerase IIa (Topo2A), an enzyme that relieves tangled chromosomes and allows one strand of DNA to pass through another to prevent entanglement during DNA transcription and replication. They have also found that BAF complexes are necessary for Topo2A to bind to chromatin and to decatenate (disentangle) DNA during cell division. BAF subunit mutations in human cancers prevent normal Topo2A function and result in entangled DNA at anaphase, which is visible as anaphase bridges. The inventors have further demonstrated that tumor cells harboring BAF subunit mutations can be identified and targeted for treatment with topoisomerase inhibitors.

The Prevalence of Mutations in the Genes Encoding Subunits of BAF Complexes in Human Cancer.

Recent exon-sequencing studies of human tumors have revealed that subunits of BAF are mutated in more than 20% of all human malignancies (Kadoch, C. et al. Proteomic and bioinformatic analysis of mammalian SWI/SNF complexes identifies extensive roles in human malignancy. *Nature Genet.* 45 (published on-line May 5, 2013); You, J. S. & Jones, P. A. *Cancer Cell* 22, 9-20 (2012)), but the mechanisms involved in tumor suppression are unclear. As described above, BAF chromatin-remodeling complexes are polymorphic assemblies that use energy provided by ATP hydrolysis to regulate transcription through the control of chromatin structure (Clapier, C. R. & Cairns, B. R. *Annu. Rev. Biochem.* 78, 273-304 (2009)) and the placement of Polycomb Repressive Complex 2 (PRC2) across the genome (Ho, L. et al. *Nature Cell Biol.* 13, 903-913 (2011); Wilson, B. G. et al. *Cancer Cell* 18, 316-328 (2010)). Several proteins dedicated to this multisubunit complex, including BRG1 [SMARCA4] and BAF250a [ARID1A], are mutated at frequencies similar to those of recognized tumor suppressors. In particular, the core ATPase BRG1 is mutated in 5-10% of childhood medulloblastomas (Parsons, D. W. et al. *Science* 331, 435-439 (2011); Pugh, T. J. et al. *Nature* 488, 106-110 (2012); Jones, D. T. W. et al. *Nature* 488, 100-105 (2012); Robinson, G. et al. *Nature* 488, 43-48 (2012)) and more than 15% of Burkitt's lymphomas (Love, C. et al. *Nature Genet.* 44, 1321-1325 (2012); Richter, J. et al. *Nature Genet.* 44, 1316-1320 (2012)).

The instant disclosure demonstrates a previously unknown function of BAF complexes in decatenating newly replicated sister chromatids, a requirement for proper chromosome segregation during mitosis. It is shown that deletion of Brg1, as well as the expression of BRG1 point mutants identified in human tumors, leads to anaphase bridge formation (in which sister chromatids linked by catenated strands of DNA) and a G2/M-phase block characteristic of the decatenation checkpoint. Endogenous BAF complexes interact directly with endogenous topoisomerase IIa (Topo2A) through BAF250a and are required for the binding of Topo2A to approximately 12,000 sites across the genome. These results demonstrate that Topo2A chromatin binding is dependent on the ATPase activity of BRG1, which is compromised in oncogenic BRG1 mutants. They indicate that the ability of Topo2A to prevent DNA entanglement at mitosis requires BAF complexes and that this activity contributes to the role of BAF subunits as tumor suppressors. This function can thus be used to identify cancer patients likely to benefit from treatment with topoisomerase inhibitors and to target treatments only to the patients so identified. Likewise, patients that are unlikely to benefit from treatment with topoisomerase inhibitors may be identified, and such treatments may be avoided in those patients. Targeted therapy to patients afflicted with these common tumors is of great medical value.

Methods for Identifying and Treating Cancer Patients

According to the instant disclosure, tumors with mutations in the genes that encode subunits of BAF complexes lead to reduced topoisomerase activity and are thus less sensitive to the actions of certain topoisomerase inhibitors than surrounding normal cells. Certain chemotherapeutic agents are characterized as topoisomerase inhibitors, but their cytotoxicity results not from topoisomerase inhibition but from the resultant DNA damage from Topo2A inhibition on DNA. Without intending to be bound by theory, such chemotherapeutic agents are therefore less effective in the treatment of cancers resulting from mutations in the BAF complex because the tumor cell is already lacking the activity of at least one allele of a specific subunit of BAF complexes which are required for Topo2A binding to DNA. Hence it follows that the tumor cell is less sensitive than the normal cells of the same individual or tumor cells from cancers that do not have BAF subunit mutations.

In one aspect, the instant disclosure thus provides methods for identifying and treating cancer patients. In certain embodiments, the methods comprise the step of obtaining a tumor sample and a non-tumor sample from the cancer patient. Ideally, the tumor sample is less sensitive to treatment with a topoisomerase inhibitor due to a decreased activity of at least one subunit of its BAF complex, and the tumor sample can therefore be distinguished from samples that are sensitive to such treatment by determining the activity of the BAF complex subunit and comparing that activity to the activity of the same BAF complex subunit in a non-tumor sample from the same cancer patient (i.e., a paired specimen).

Accordingly, in preferred embodiments, the tumor sample is a colorectal cancer, a clear-cell ovarian cancer, a serous ovarian cancer, a pancreatic cancer, a gastric cancer, a bladder cancer, a hepatocellular cancer, a renal cancer, a squamous cell carcinoma, a breast cancer, a medulloblastoma, a glioma, a melanoma, a lung cancer, a prostate cancer, a sarcoma, a malignant rhabdoid tumor, or a hematologic malignancy. These cancers have recently been shown to contain prevalent mutations in critical subunits of the BAF complex. See, e.g., Kadoch, C. et al. Proteomic and bioinformatic analysis of mammalian SWI/SNF complexes identifies extensive roles in human malignancy. *Nature Genet*. v. 45 (published on-line May 5, 2013); Barbieri et al *Nat Genet*. 44(6):685-9 (2012); Versteege et al. *Nature*. 394(6689):203-6 (1998); Kadoch and Crabtree *Cell* 153:71-85 (2013).

In more preferred embodiments, the tumor sample is a colorectal cancer, a clear-cell ovarian cancer, a pancreatic cancer, a gastric cancer, a bladder cancer, a hepatocellular cancer, a renal cancer, a breast cancer, a medulloblastoma, a lung cancer, or a hematologic malignancy.

In other more preferred embodiments, the tumor sample is a prostate cancer, a sarcoma, or a malignant rhabdoid tumor. See Barbieri et al. *Nat Genet*. 44(6):685-9 (2012); Versteege et al. *Nature*. 394(6689):203-6 (1998); Kadoch and Crabtree *Cell* 153:71-85 (2013).

In certain embodiments, the methods of the instant disclosure comprise the step of determining the activities of at least one BAF subunit in the tumor sample and in the non-tumor sample. Such activities are typically determined using standard biochemical or molecular biological techniques.

For example, in some embodiments, a portion of the gene encoding the BAF subunit is sequenced in the tumor sample and in the non-tumor sample to identify a mutation in the gene. As described in more detail in Example 1, such mutations in the tumor sample are in some instances associated with a decreased activity of the BAF subunit.

As used herein, a mutation may include any genetic modification of a gene. For example, such modifications may include translocations, point mutations, as well as insertions and deletions of any length, including gene deletions. The mutations may occur in coding regions or non-coding regions of the gene, and multiple mutations may be present within a given gene of interest.

Sequencing the gene, or portion of the gene, encoding a BAF subunit may be performed by any standard technique, as would be understood by those of ordinary skill in the art, for example using the approaches described in detail in references cited in the attached Examples. In addition, deep sequencing methodology may be of use in determining activities of the BAF subunits according to the instant methods. Accordingly, deep sequencing, i.e., sequencing the same region multiple times, may be of use in identifying mutations within the BAF subunits, because normal cell contamination is common in biopsy samples. In this regard, sequencing depth refers to the number of times a single base within the genome is sequenced.

In some embodiments, transcription of the gene encoding a BAF subunit is measured in order to determine the activity of the BAF subunit. For example, decreased levels of transcription or decreased stability of the resulting transcript are associated with a decreased activity of the BAF subunit. Analysis of the RNA transcripts may be performed by standard laboratory techniques, as would be understood by those of ordinary skill in the art.

In other embodiments, protein expression of a BAF subunit is measured in order to determine the activity of the BAF subunit. For example, decreased levels of protein expression or decreased stability of the resulting protein are associated with a decreased activity of the BAF subunit. See Sigauke et al. *Mod. Pathol*. 19(5):717-725 (2006); Haberler et al. *Am. J. Surg. Pathol*. 30(11):1462-8 2006). Analysis of such protein expression, for example by immunoassay or other biochemical methods, may be performed using any appropriate technique. In particular, the analysis of protein expression by immunohistochemistry on pathological specimens is of use in the practice of the instant methods.

For certain subunits of BAF, for example ARID1A, point mutations can lead to a loss of expression, and the protein may also be independently downregulated even in the absence of mutation. See Lichner et al *Am. J. Pathol*. 182:1163-1170 (2013); Wiegand et al. *J. Pathol*. 224:328-333 (2011). Alternative techniques for assessing the activity of a BAF subunit in a tumor sample, such as, for example, the above techniques for measuring gene and/or protein expression, may thus be desirable in addition to, or alternatively to, techniques that assess activity by sequencing a portion of the gene encoding the BAF subunit.

In some embodiments of the invention, the activities of the BAF subunit are determined by measuring post-translational modification of the BAF subunit. Non-limiting examples of post-translational modifications include covalent modification of amino acid side chains, for example by phosphorylation, acylation, alkylation, isoprenylation, glycosylation, and the like, polypeptide cleavage, disulfide bond formation, and other such modifications, as would be understood by those of ordinary skill in the art. Such modification of BAF subunits may decrease the activity of the modified subunit and thus potentially alter the likelihood of effectiveness of treatment of patient with a topoisomerase inhibitor.

In yet still other embodiments, decatenation of DNA by topoisomerase IIa is measured in order to determine the activity of the BAF subunit. For example, decreased decatenation of DNA is associated with a decreased activity of the BAF subunit. Measurement of decatenation may be performed, for example, as described in the attached Example 1, or by any other appropriate technique.

In preferred embodiments of the instant methods, the BAF subunit whose activity is determined in the method is a component of the BAF complex that, when modified, causes an altered sensitivity of the cells to treatment with a topoisomerase inhibitor. Identification of such modified components in tumor samples guides the effective treatment in appropriate patients with topoisomerase inhibitors.

According to highly preferred embodiments, the BAF subunit is encoded by SMARCA4, SMARCA2, ARID1A, ARID1B, ARID2, PBRM1, BCL11A, BCL11B, BCL7A, BCL7B, BCL7C, SMARCB1, SMARCD1, SMARCD2, SMARCD3, SMARCC1, SMARCC2, PHF10, DPF1, DPF2, DPF3, ACTL6A, ACTL6B, BRD9, SS18, or SMARCE1. These genes are known to be defective at high frequencies in a wide variety of cancers and thus serve as targets for therapies using topoisomerase inhibitors.

In even more highly preferred embodiments, the BAF subunit is encoded by SMARCA4, ARID1A, ARID1B, ARID2, PBRM1, BCL11A, BCL11B, BCL7A, or SMARCB1.

In some embodiments of the above methods, a comparison of the activities of the BAF subunit in the tumor sample and in the non-tumor sample determines that the likelihood of effectiveness of treatment with a topoisomerase inhibitor is decreased. For example, as demonstrated in Examples 2 and 3 below, cell lines carrying mutations in BAF subunits display a decreased sensitivity to the topoisomerase inhibitors etoposide and doxorubicin. Without intending to be bound by theory, it is believed that tumor cells having decreased activity of a BAF subunit may have an altered sensitivity to topoisomerase inhibitors that cause double-stranded breaks in genomic DNA. Non-limiting examples of such inhibitors include etoposide, teniposide, doxorubicin, daunorubicin, mitoxantrone, amsacrine, ellipticine, and epirubicin. In particular, it is believed that such tumor cells may have a decreased sensitivity to these inhibitors as a result of the decreased activity of a BAF subunit. Accordingly, in embodiments involving the treatment of a patient, the methods include the step of not treating the patient with the topoisomerase inhibitor if the likelihood of effectiveness of treatment is decreased.

In some embodiments of the above methods, a comparison of the activities of the BAF subunit in the tumor sample and in the non-tumor sample determines that the likelihood of effectiveness of treatment with a topoisomerase inhibitor is increased or unchanged. For example, as demonstrated in Example 2 below, cell lines carrying mutations in BAF subunits display no difference in the sensitivity to the topoisomerase inhibitor ICRF-193. Without intending to be bound by theory, it is believed that the effectiveness of topoisomerase inhibitors not causing double-stranded breaks in genomic DNA may be less affected by altered activities of BAF subunits. Non-limiting examples of such inhibitors include aurintricarboxylic acid, HU-331, epigallocatechin gallate, genistein, quercetin, resveratrol, and ICRF-193. Tumor cells with decreased activity of a BAF subunit may therefore remain sensitive to these inhibitors. Accordingly, in embodiments involving the treatment of a patient, the methods include the step of treating the patient with the topoisomerase inhibitor if the likelihood of effectiveness of treatment is increased or unchanged.

In some embodiments, the methods of the instant disclosure involve determining the activities of at least two BAF subunits in the tumor sample and in the non-tumor sample, wherein a decreased activity of at least one BAF subunit in the tumor sample indicates an altered likelihood of effectiveness of treatment with a topoisomerase inhibitor. In more specific embodiments, the methods involve determining the activities of at least five, ten, or even more BAF subunits in the tumor sample and in the non-tumor sample, wherein a decreased activity of at least one BAF subunit in the tumor sample indicates an altered likelihood of effectiveness of treatment with a topoisomerase inhibitor. In some embodiments, a decreased activity of at least two BAF subunits in the tumor sample, or even more BAF subunits in the tumor sample, indicate an altered likelihood of effectiveness of treatment with a topoisomerase inhibitor.

In yet another aspect, the instant disclosure provides further methods for treating cancer patients. In these methods, an analysis of a tumor sample is requested for the cancer patient. Such a request may be made, for example, by the physician treating the patient, by the hospital where the treatment occurs, or by another facility responsible for the patient's care.

The results shown in FIGS. 11A-C and 12A-B demonstrate that, in general, tumors with a decreased activity of a BAF subunit, in these examples due to a mutation or loss of protein expression, will be resistant to topoisomerase inhibitors, perhaps because Topo2a cannot bind DNA to perform its function in the presence of Topo2a inhibitors. However, mutations in other subunits might allow Topo2a to bind to DNA yet prevent its function on DNA. In these cases, greater sensitivity to topoisomerase inhibitors may be observed. In some cases, the sensitivity of tumors with altered BAF subunit activity may display unchanged sensitivity to topoisomerase inhibitors.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following Examples, which are included herewith for purposes of illustration only and are not intended to be limiting of the invention.

EXAMPLES

Example 1

BAF Complexes Facilitate Decatenation of DNA by Topoisomerase IIα

Using Brg1$^{floxed/floxed}$ (Brg1$^{fl/fl}$) actin-creER embryonic stem cells (ESCs), it was observed that tamoxifen-induced deletion of Brg1 (Brg1$^{fl/fl}$(ERD)) results in the appearance of DNA bridges during anaphase (FIG. 1A). This phenotype is characteristic of a deficiency in Topo2A function, which normally resolves DNA catenanes that develop during transcription and replication. Carpenter, A. J. & Porter, A. C. Mol. Biol. Cell 15, 5700-5711 (2004). It was determined that the frequency of anaphase bridges in Brg1$^{fl/fl}$(ERD) cells is similar to that of cells deficient in other putative tumor suppressors that regulate Topo2A function, including BRCA1, RANBP2 and RECQL5 (Lou, Z., Minter-Dykhouse, K. & Chen, J. Nature Struct. Mol. Biol. 12, 589-593 (2005); Dawlaty, M. M. et al. Cell 133, 103-115 (2008); Ramamoorthy, M. et al. Nucleic Acids Res. 40, 1621-1635 (2012)) (FIG. 1A).

Figure 5A:
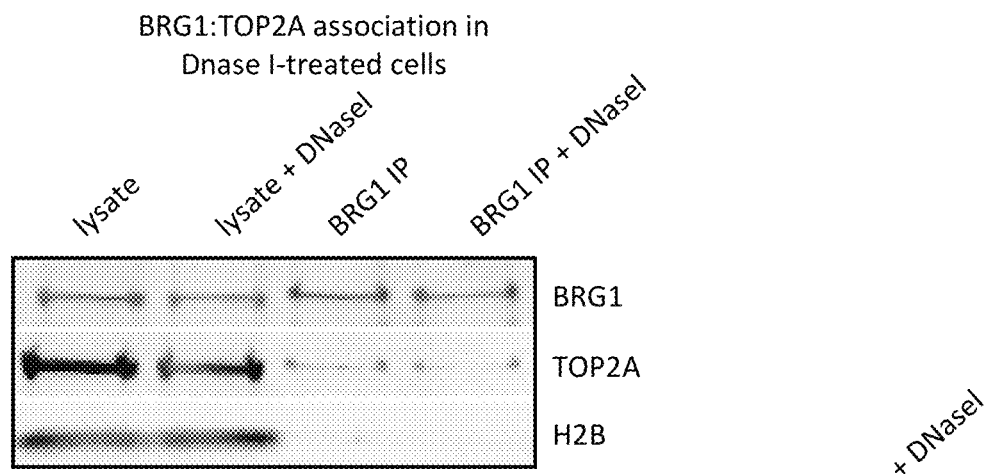
FIG. 5A-FIG. 5E. Characteristics of the BRG1:Topo2A association.
Figure 5B:
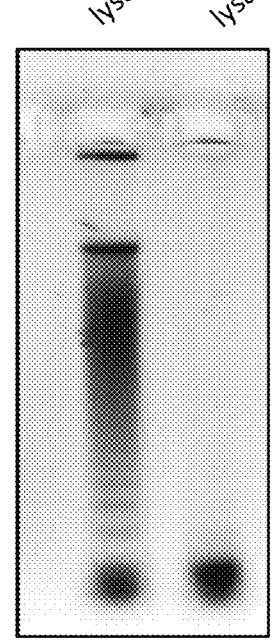
Figure 5C:
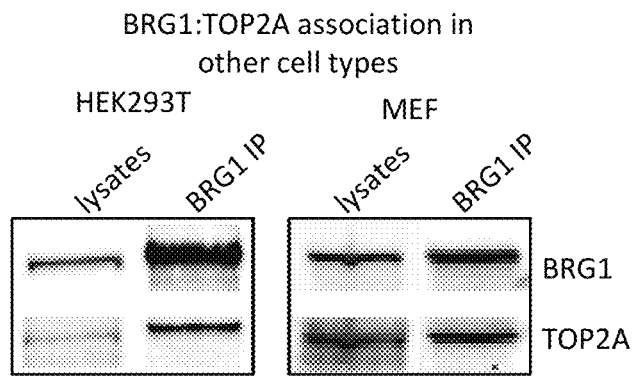

In previous studies, peptides from Topo2A in mass spectrometric analysis of endogenous BAF complexes were recovered. Ho, L. et al. Proc. Natl Acad. Sci. USA 106, 5181-5186 (2009). Immunoprecipitation of BAF complexes with antibodies to BRG1 recovered Topo2A and, conversely, immunoprecipitation of Topo2A revealed BRG1 (FIG. 1B). This association is not dependent on DNA (FIG. 5A, B). This association was detected in several additional cell types, including mouse embryonic fibroblasts (MEFs) and human embryonic kidney (HEK293T) cells (FIG. 5C).

Figure 5D:
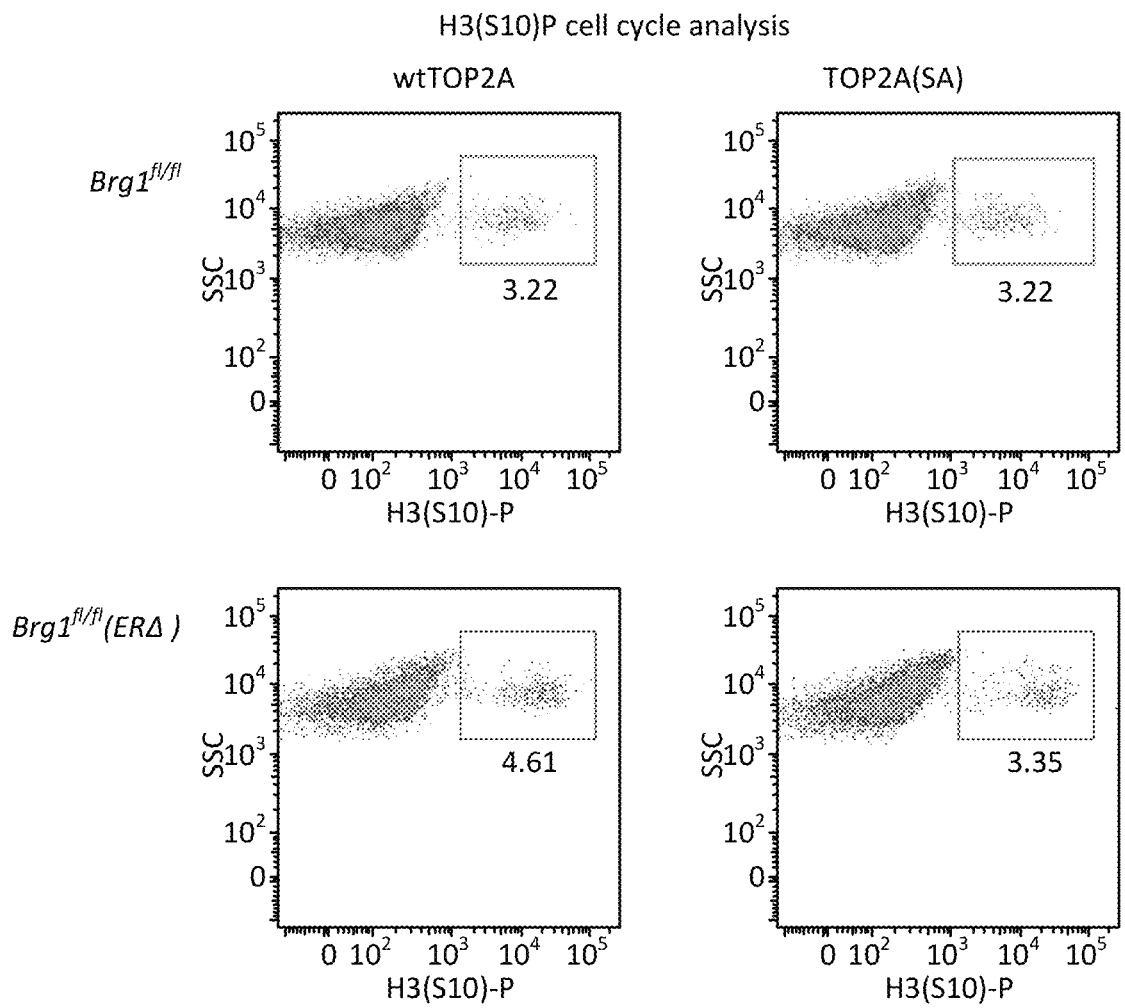
Figure 5E:
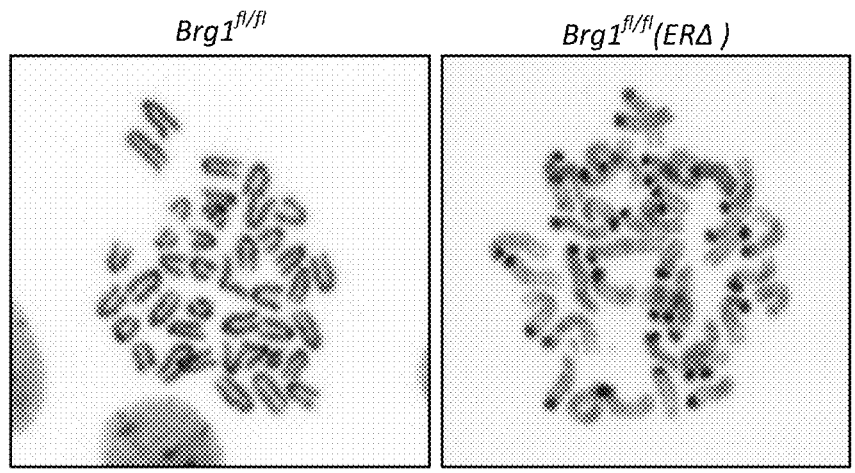

Failure of Topo2A to resolve catenated DNA leads to slow progression through the G2/M phase of the cell cycle. Johnson, M., Phua, H. H., Bennett, S. C., Spence, J. M. & Farr, C. J. *Nucleic Acids Res.* 37, e98 (2009). To better understand the mitotic defect in BRG1-deficient cells, Brg1$^{fl/fl}$ and Brg1$^{fl/fl}$(ERD) cells in G1/S were synchronized using double-thymidine block. After release, Brg1$^{fl/fl}$ and Brg1$^{fl/fl}$(ERD) cells transited through the cell cycle at the same rate until reaching G2/M, where the Brg1$^{fl/fl}$(ERD) cells exhibited a substantial delay (FIG. 1C). In asynchronously dividing cells, this delay resulted in a 1.5- to twofold increase in Brg1$^{fl/fl}$(ERD) cells in G2/M (FIG. 1D), similar to the treatment of cells with the topoisomerase II inhibitor ICRF-193. Downes, C. S. et al. *Nature* 372, 467-470 (1994). Caffeine, an inhibitor of ATM/ATR, forces cells through an ICRF-193-induced decatenation checkpoint (Downes, C. S. et al. *Nature* 372, 467-470 (1994)) and similarly overrides the G2/M arrest in Brg1$^{fl/fl}$(ERD) cells (FIG. 1D). Furthermore, expression of Topo2A(S1524A); hereafter Topo2A (SA), which fails to recruit MDC1 to chromatin upon initiation of the decatenation checkpoint (Luo, K., Yuan, J., Chen, J. & Lou, Z. *Nature Cell Biol.* 11, 204-210 (2009)), alleviated the cell cycle delay, suggesting that Brg1$^{fl/fl}$(ERD) cells arrest due to activation of the decatenation checkpoint (FIG. 1E and FIG. 5D). Finally, chromosomes from Brg1$^{fl/fl}$(ERD) cells are significantly longer than chromosomes from Brg1$^{fl/fl}$ cells (FIG. 1F and FIG. 5E), a defect observed in Topo2A-deficient cells due to its role in chromosome condensation. Carpenter, A. J. & Porter, A. C. *Mol. Biol. Cell* 15, 5700-5711 (2004); Sakaguchi, A. & Kikuchi, A. *J. Cell Sci.* 117, 1047-1054 (2004). These data indicate that Brg1 deletion resembles the mitotic defects observed with chemical inhibition and/or knockdown of Topo2A. Carpenter, A. J. & Porter, A. C. *Mol. Biol. Cell* 15, 5700-5711 (2004); Johnson, M., Phua, H. H., Bennett, S. C., Spence, J. M. & Farr, C. J. *Nucleic Acids Res.* 37, e98 (2009); Downes, C. S. et al. *Nature* 372, 467-470 (1994); Sakaguchi, A. & Kikuchi, A. *J. Cell Sci.* 117, 1047-1054 (2004).

Figure 2B:
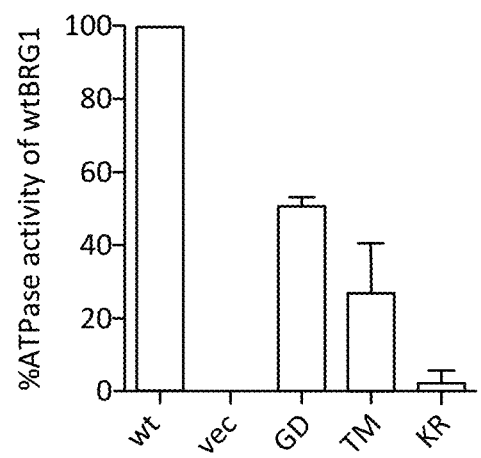
Figure 6A:
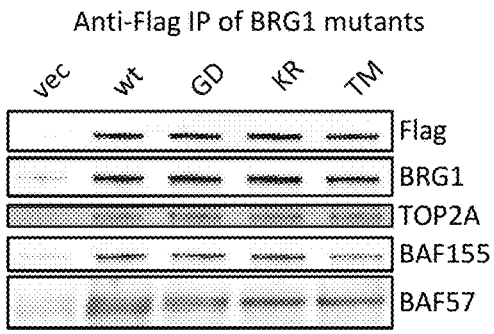
FIG. 6A-FIG. 6D. Analysis of the BRG1 somatic mutations found in medulloblastoma (MB).
Figure 6B:
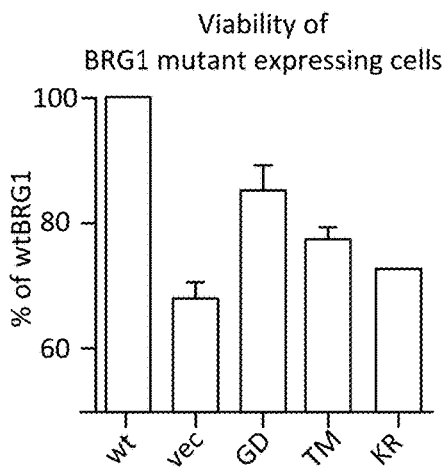

The oncogenic point mutants of BRG1 found in medulloblastoma and Burkitt's lymphoma (BRG1(G1232D); hereafter BRG1(GD) and BRG1(T910M); hereafter BRG1 (TM)) (Parsons, D. W. et al. *Science* 331, 435-439 (2011); Pugh, T. J. et al. *Nature* 488, 106-110 (2012); Jones, D. T. W. et al. *Nature* 488, 100-105 (2012); Robinson, G. et al. *Nature* 488, 43-48 (2012); Love, C. et al. *Nature Genet.* 44, 1321-1325 (2012); Richter, J. et al. *Nature Genet.* 44, 1316-1320 (2012)) were investigated by expressing FLAG-tagged versions in Brg1$^{fl/fl}$ cells (FIG. 2A). The BRG1 mutants were incorporated into the BAF complex normally and did not alter the composition of the complex (FIG. 6A). Although the T910M mutation is located in the ATP-binding pocket of BRG1, the G1232D mutation is downstream of the helicase superfamily c-terminal (HELICc) domain and thus not obviously involved in ATP turnover (FIG. 2A). Subjecting BAF complexes containing BRG1(GD), BRG1(TM), wild-type BRG1 (hereafter wtBRG1), or BRG1(K798R) (hereafter BRG1(KR)) (Khavari, P. A., Peterson, C. L., Tamkun, J. W., Mendel, D. B. & Crabtree, G. R. *Nature* 366, 170-174 (1993))—the ATPase-dead point mutant of BRG1—to an assay for ATPase activity revealed that both cancer mutants are significantly compromised in ATPase activity, although not as profoundly as BRG1(KR) (FIG. 2B). BRG1(TM) is more severely compromised than BRG1 (GD), which correlated with the viability of the respective cell line (FIG. 6B).

Figure 2C:
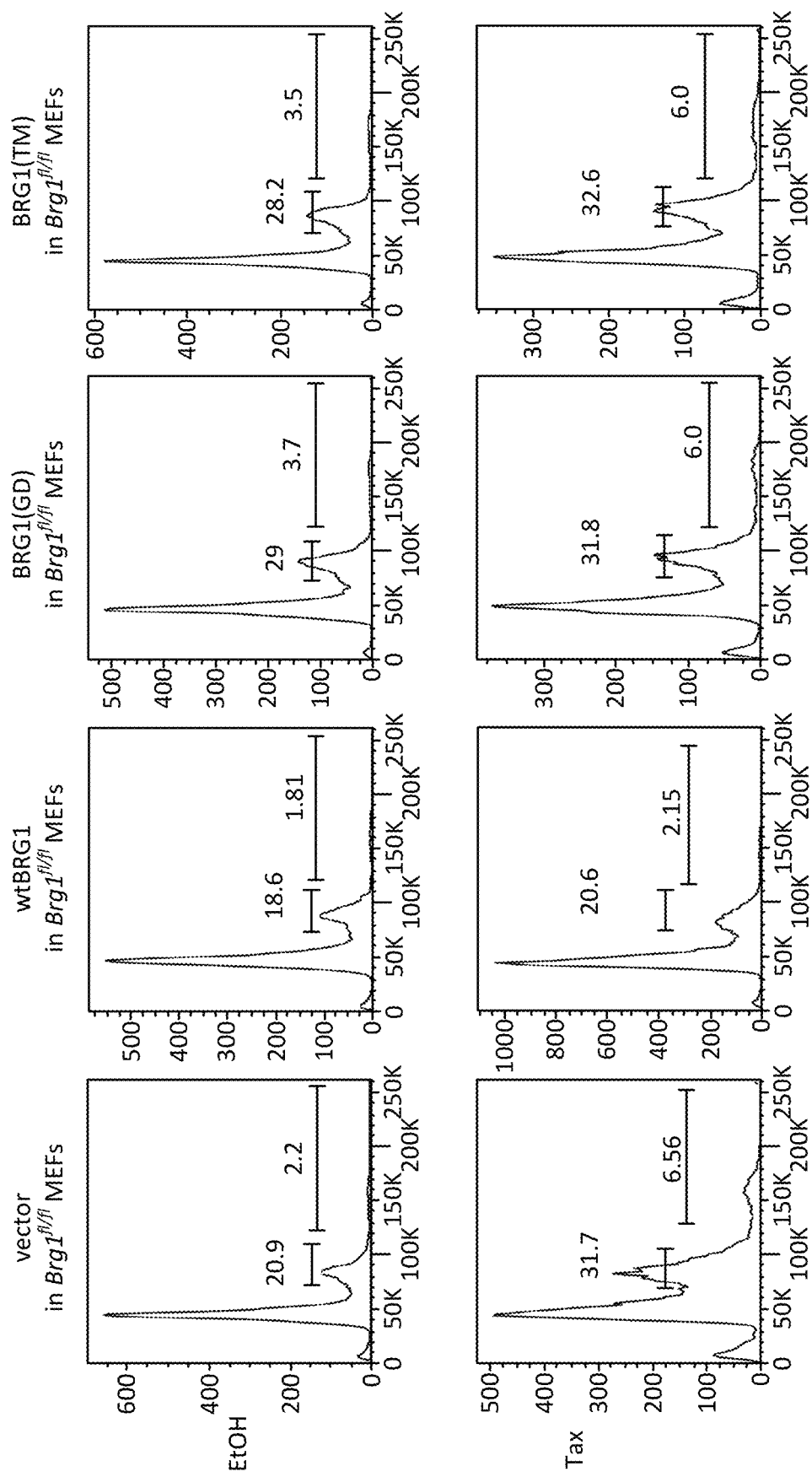

Cells expressing BRG1(GD) and BRG1(TM), but not wtBRG1, display increases in the percentage of G2/M cells and the incidence of anaphase bridges similar to that of Brg1$^{fl/fl}$(ERD) cells (FIG. 2C, D). Importantly, expression of the mutants in the presence of endogenous BRG1 gives similar increases, although less severe, in G2/M percentage and anaphase bridge incidence compared to vector cells (FIG. 2C, D). The dominant nature of these mutants on cell cycle and anaphase bridge formation suggests that medulloblastomas with both heterozygous and homozygous mutations in BRG1 have these mitotic defects.

Figure 6C:
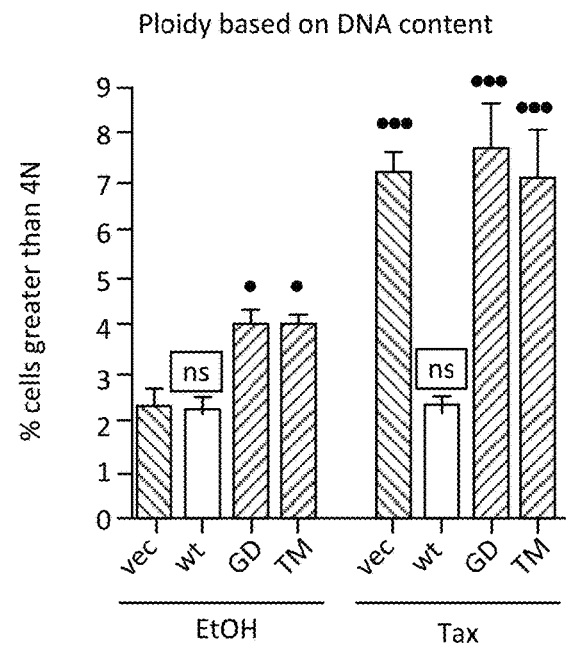

To explore whether the increase in anaphase bridges contributes to increased chromosome instability as it does in Topo2A-deficient cells (Carpenter, A. J. & Porter, A. C. *Mol. Biol. Cell* 15, 5700-5711 (2004); Johnson, M., Phua, H. H., Bennett, S. C., Spence, J. M. & Farr, C. J. *Nucleic Acids Res.* 37, e98 (2009)), ploidy in the BRG1 mutant cell lines were analyzed. Expression of BRG1(GD) or BRG1(TM) results in a significant increase in cells with >4 n DNA content in both ethanol- and tamoxifen-treated cells (FIG. 2C and FIG. 6C). A significant increase in the number of BRG1(GD)- and BRG1(TM)-expressing cells with abnormal chromosome number in metaphase spreads from both ethanol- and tamoxifen-treated samples (FIG. 2E) was also observed. These data indicate that the G1232D and T910M mutations in BRG1 can contribute to chromosome instability as a result of deficiencies in Topo2A function.

Figures 2D, 2E, 2F:
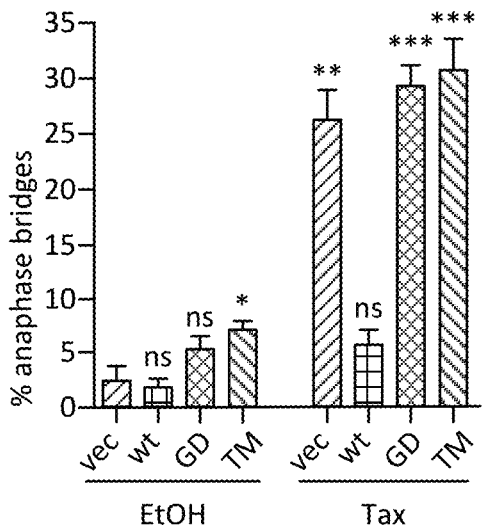
Figure 6D:
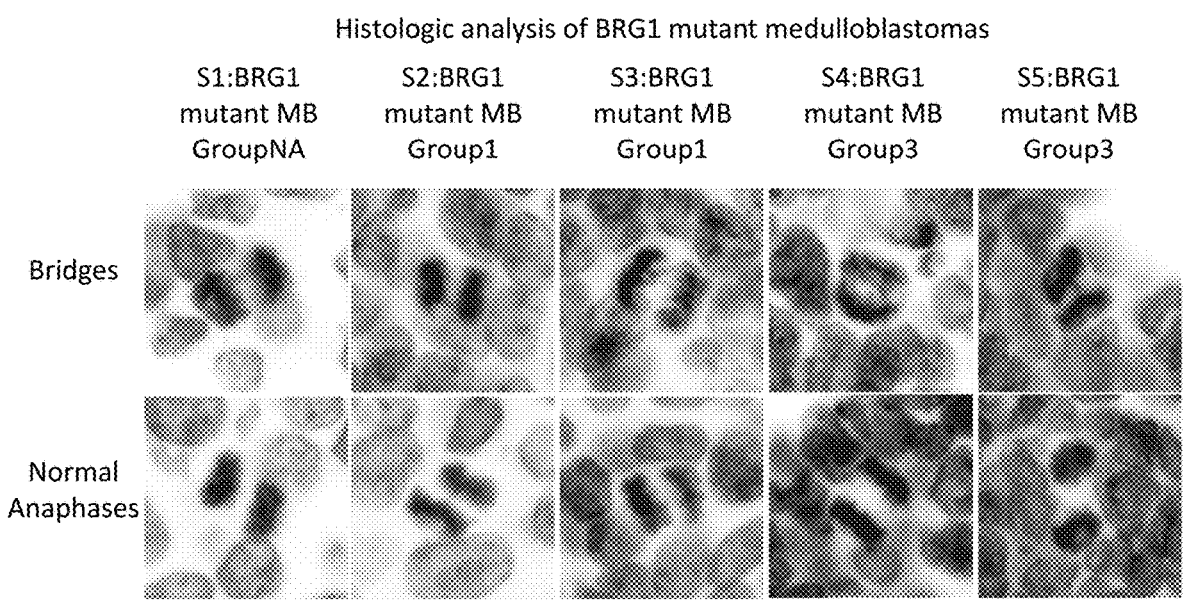
Figure 7C:
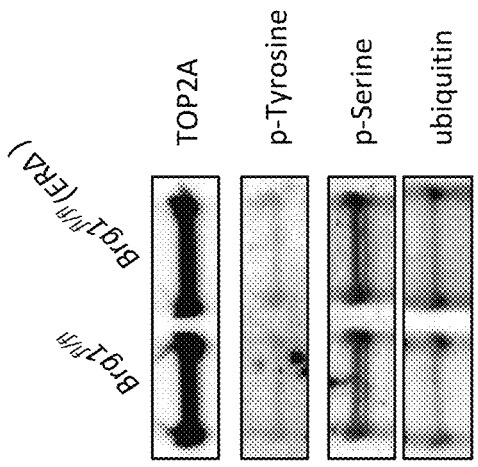
FIG. 7A-FIG. 7F. Topo2A levels, post-translational modifications, and activity are unchanged in Brg1$^{fl/fl}$(ERΔ) ESCs.
Figure 7E:
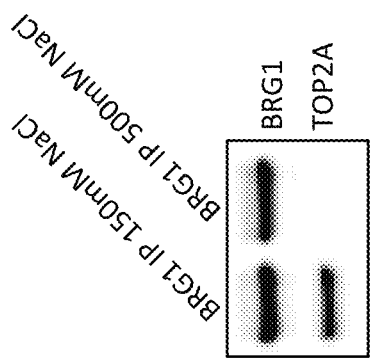
Figure 7B:
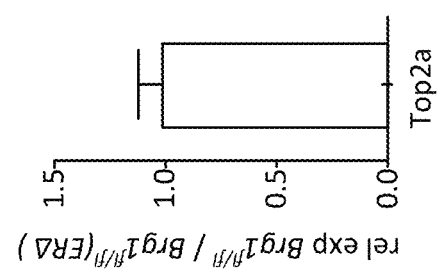
Figure 7A:
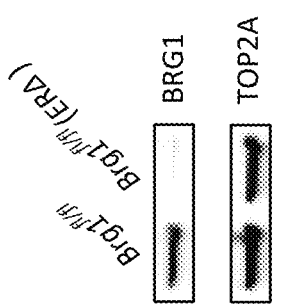
Figure 7D:
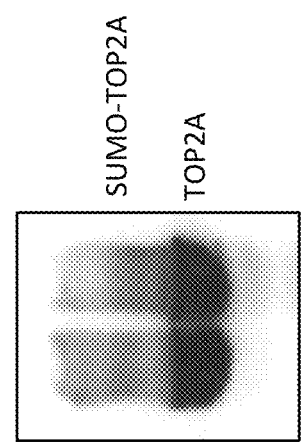
Figure 7F:
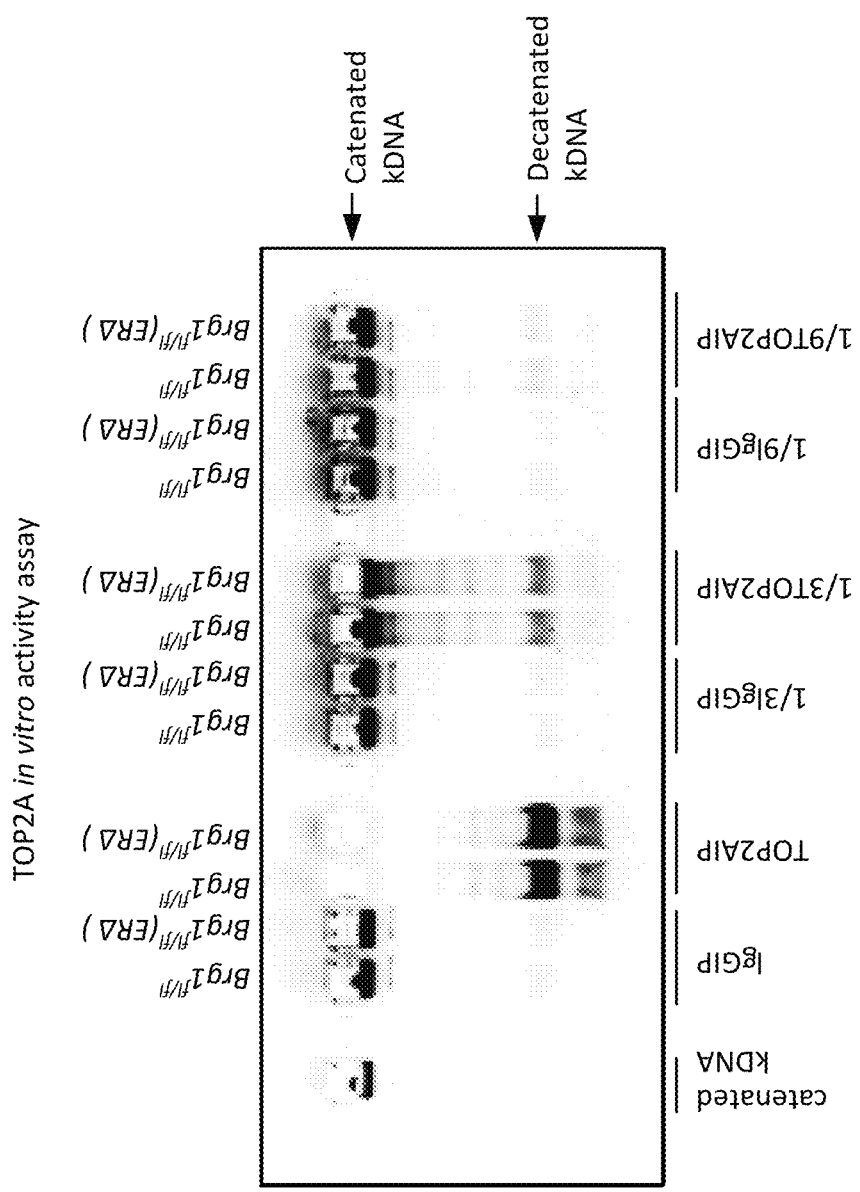
Figure 8A:
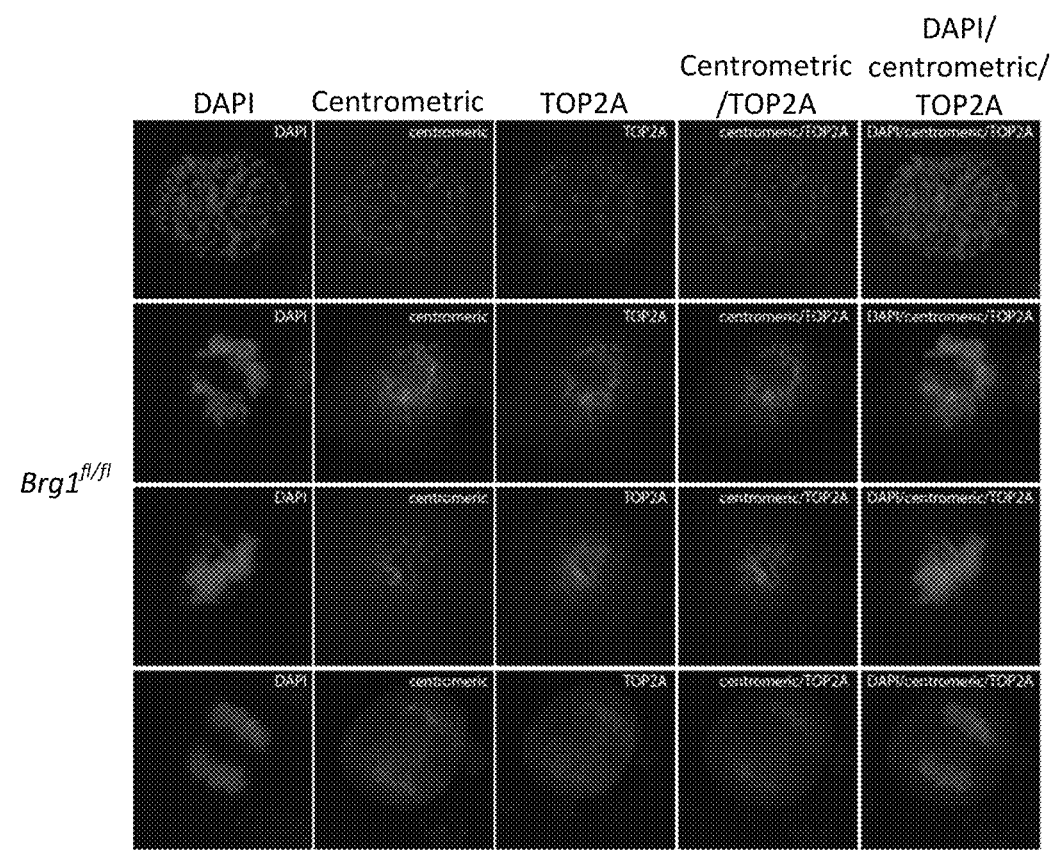
FIG. 8A and FIG. 8B. Topo2A location is unchanged in Brg1$^{fl/fl}$(ERΔ) MEFs.
Figure 8A:
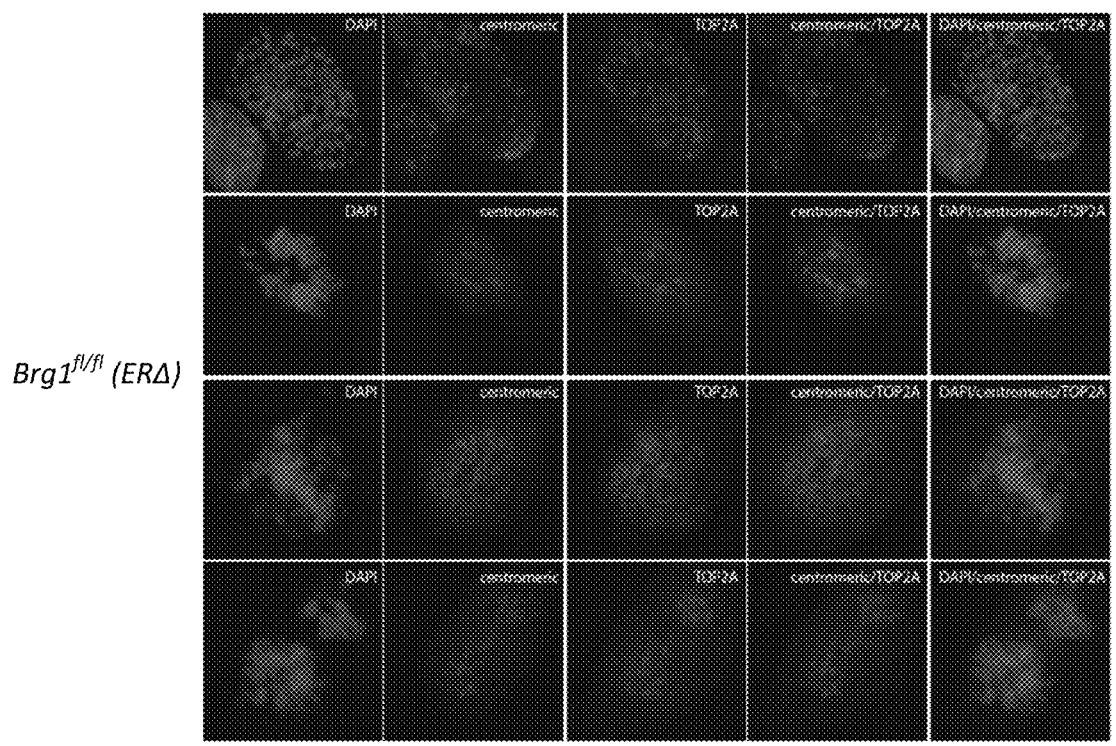
Figure 8B:
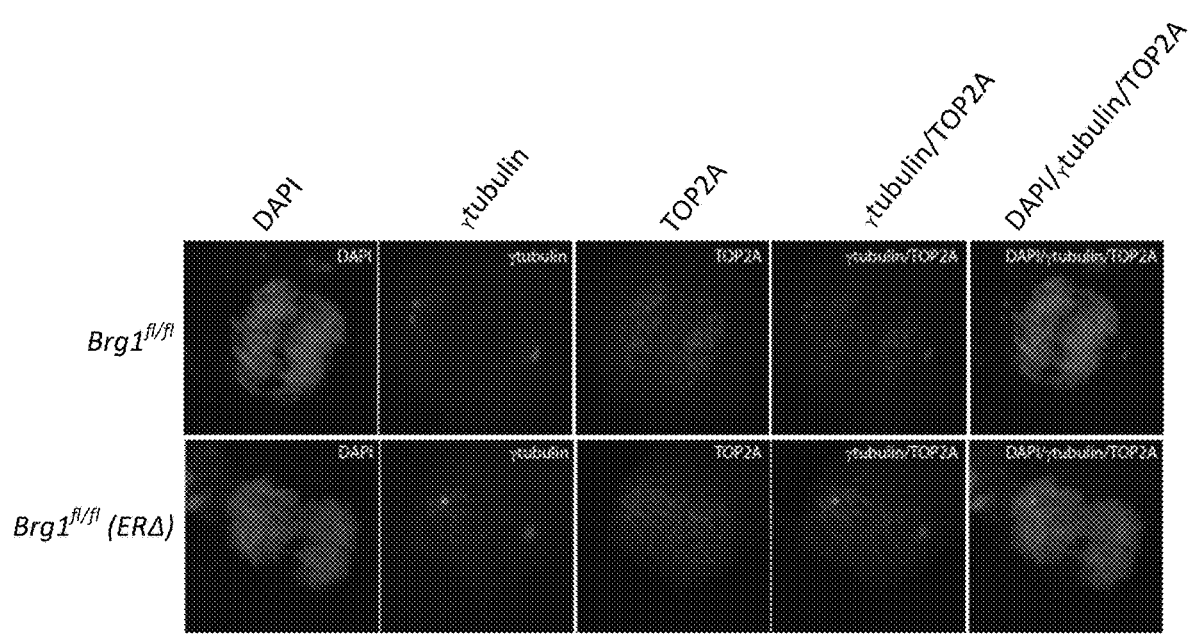

Several BRG1 mutant medulloblastomas were collected to determine whether the effects of Topo2A deficiency can be observed in primary tumors. An increased proportion of anaphase bridges in each of five histologic samples from BRG1 mutant tumors relative to controls was observed, suggesting these tumors have decatenation defects (FIG. 2F and FIG. 6D). Aneuploidy is common in medulloblastoma and ranges from the partial gain or loss of single chromosomes to full tetraploidy. Jones, D. T. W. et al. *Nature* 488, 100-105 (2012); Kool, M. et al. *Acta Neuropathol.* 123, 473-484 (2012); Northcott, P. A. et al. *Nature Rev. Cancer* 12, 818-834 (2012). However, a recent study showed that the relative rate of tetraploidy of 5 BRG1 mutant tumors was similar to that of 15 BRG1 wild-type tumors. Jones, D. T. W. et al. *Nature* 488, 100-105 (2012). Additional sample characterization will be necessary to definitively assess whether BRG1 mutation causes mitotic defects through insufficient Topo2A function in medulloblastomas.

Microarray analysis of Brg1$^{fl/fl}$ and Brg1$^{fl/fl}$(ERD) ESCs indicated that BRG1-dependent genes are not enriched for Gene Ontology terms related to DNA damage or repair. Ho, L. et al. *Proc. Natl Acad. Sci. USA* 106, 5187-5191 (2009). Additionally, no alterations in the abundance, post-translational modifications, cellular localization, or in vitro enzymatic activity of Topo2A in Brg1$^{fl/fl}$(ERD) cells were found (FIGS. 7A-F and 8A-B). To test whether purified BAF complexes could enhance the enzymatic activity of recombinant Topo2A, the standard in vitro kinetoplast DNA-based decatenation assay was used. Immobilized BAF complexes increased the enzymatic activity of Topo2A (FIG. 9A); however, immunoprecipitated BRG1 mutant BAF complexes also enhanced Topo2A activity, as did immunoprecipitated SUZ12-containing PRC2 complexes, indicating a nonspecific activity on a bare DNA template (Stros, M., Bacikova, A., Polanska, E., Stokrova, J. & Strauss, F. *Nucleic Acids Res.* 35, 5001-5013 (2007)) that does not reflect the in vivo observations. The BRG1 mutants did, however, reduce the association between Topo2A and chromatin, such that more Topo2A remained associated with chromatin after high salt wash in wtBRG1 cells than in BRG1(TM), BRG1(GD) and vector cells (FIG. 3A and FIG. 9B, C). Reduced binding of Topo2A to chromatin would be expected to compromise Topo2A function and could represent an inability of Topo2A to associate with substrate DNA during decatenation.

To identify defined regions of Topo2A binding across the genome, a Topo2A chromatin immunoprecipitation combined with massively parallel DNA sequencing (ChIP-seq) in Brg1$^{fl/fl}$ and Brg1$^{fl/fl}$(ERD) cells was performed. Very few peaks were recovered using traditional ChIP methods, so etoposide, a small molecule that freezes Topo2A in a covalent complex with DNA during the enzymatic process was used, thereby identifying sites of active Topo2A cleavage. Sano, K., Miyaji-Yamaguchi, M., Tsutsui, K. M. & Tsutsui, K. *PLoS ONE* 3, e4103 (2008). 16,591 Topo2A peaks were recovered in Brg1$^{fl/fl}$ cells and 4,623 Topo2A peaks were recovered in Brg1$^{fl/fl}$(ERD) cells, demonstrating the contribution of BRG1 to Topo2A binding (FIG. 3B). Almost two-thirds of the Topo2A Brg1$^{fl/fl}$ peaks are DNase-I-hypersensitive, consistent with the preference of Topo2A for nucleosome-free DNA. Capranico, G., Jaxel, C., Roberge, M., Kohn, K. W. & Pommier, Y. *Nucleic Acids Res.* 18, 4553-4559 (1990). An example reflecting these trends is shown in FIG. 3C. Topo2A binding by ChIP-quantitative PCR (qPCR) was confirmed at 14 BRG1-dependent and 10 BRG1-independent sites in Brg1$^{fl/fl}$ and Brg1$^{fl/fl}$(ERD) cells (FIG. 3D). In addition, it was determined that Topo2A binding is mitigated in BRG1(TM) and BRG1(GD) mutant Brg1$^{fl/fl}$(ERD) cells at BRG1-dependent sites (FIG. 3E). This is not the result of reduced binding of the BRG1 mutants to chromatin, as BRG1(TM) and BRG1(GD) bind similarly to wtBRG1 at these sites (FIG. 3F). Given that the BRG1(TM) and BRG1(GD) mutants display reduced ATPase activity, these data implicate a role for the ATP-dependent accessibility activity of BAF complexes in Topo2A binding and function across the genome, a function previously identified for yeast protein Snf5 in transcription. Sperling, A. S., Jeong, K. S., Kitada, T. & Grunstein, M. *Proc. Natl Acad. Sci. USA* 108, 12693-12698 (2011).

Figure 4A:
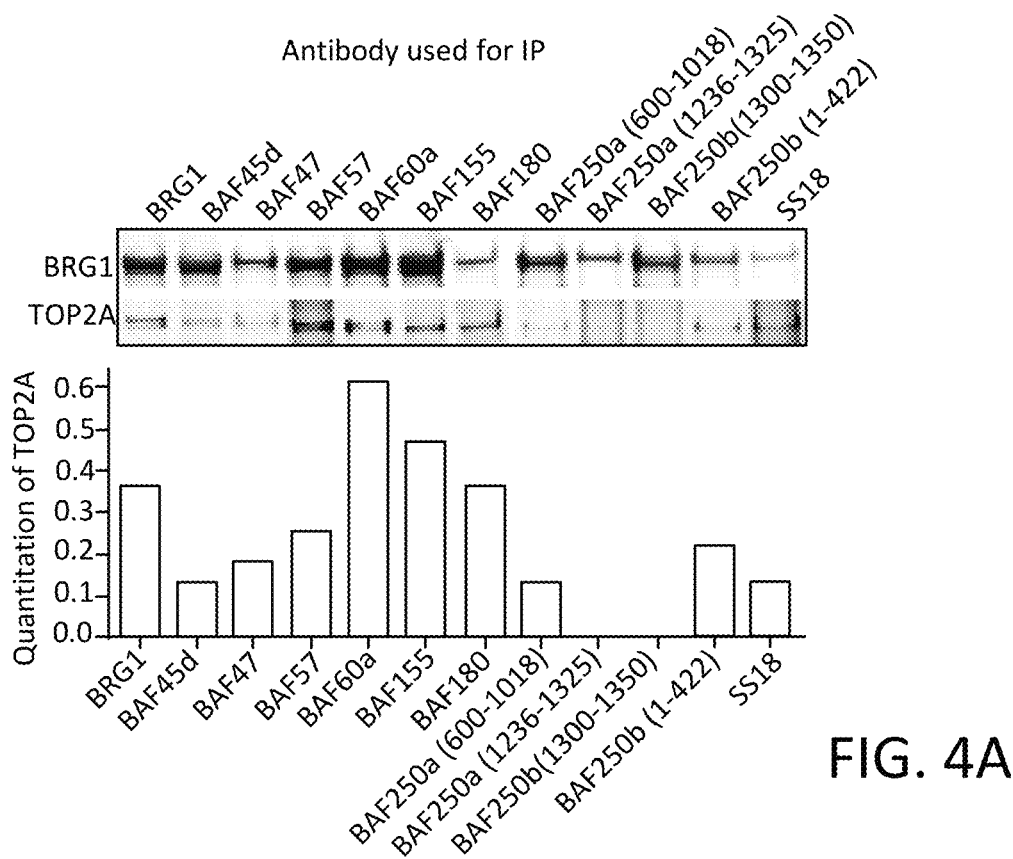
Figure 4B:
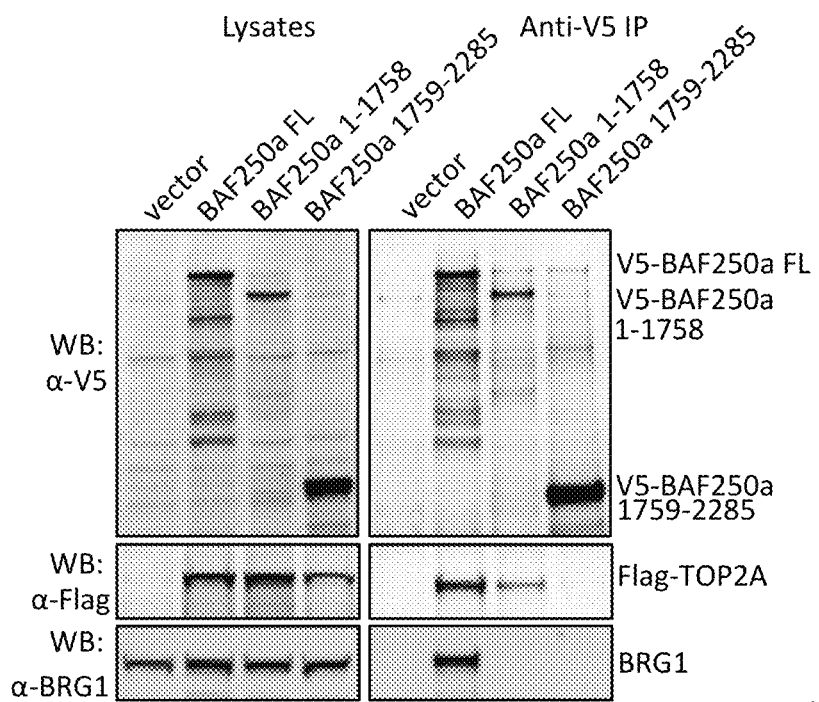

Owing to the dedicated nature of subunits within BAF complexes, Topo2A could be interacting with any BAF subunit. Indeed, Topo2A was precipitated with antibodies to several dedicated subunits as determined by glycerol gradient centrifugation analysis (FIG. 4A and FIG. 10A). Quantification of the precipitated Topo2A revealed that little Topo2A was recovered after immunoprecipitation with antibodies raised against BAF250a (amino acids 1236-1325) and BAF250b (also known as ARID1B; amino acids 1300-1350), whereas other antibodies immunoprecipitated Topo2A well (FIG. 4A). It was reasoned that the BAF250a/b antibody might disrupt the interaction between Topo2A and the BAF complex if Topo2A bound directly to BAF250a/b. Indeed, Topo2A associated with full-length BAF250a and BAF250a (amino acids 1-1758), but not BAF250a (amino acids 1759-2285) in a heterologous expression system (FIG. 4B). This interaction is independent of BRG1 because BRG1 in co-precipitates of BAF250a (1-1758) and Topo2A was unable to be detected. Furthermore, the association between Topo2A and BRG1 was lost upon knockdown of BAF250a, with the most severe knockdown resulting in the most severe loss of association (FIG. 4C and FIG. 10B). To determine whether the interaction between Topo2A and BAF250a was physiologically relevant, BAF250a in MEFs was knocked down, and frequencies of anaphase bridges and G2/M delay similar to knockdown of Brg1 or Top2a were observed (FIG. 4D, E and FIG. 10C, D). These data indicate that Topo2A associates with BRG1 through a direct interaction with BAF250a.

These studies point to a new role for ATP-dependent chromatin remodeling in decatenating DNA. Reduced decatenation in vivo is revealed by the frequency of anaphase bridges and an increase in the number of cells in G2/M upon deletion of BRG1 or expression of the tumor-associated T910M and G1232D BRG1 mutants (FIGS. 1A, D and 2C, D). Although mitotic defects have been noted in cells lacking BRG1, the cause of these defects was unclear. Bourgo, R. J. et al. *Mol. Biol. Cell* 20, 3192-3199 (2009). In addition to BRG1, loss of BAF250a also results in decatenation defects (FIG. 4D, E), which could reflect the high incidence of mutations in BRG1 and BAF250a in human tumors. Kadoch, C. et al. Proteomic and bioinformatic analysis of mammalian SWI/SNF complexes identifies extensive roles in human malignancy. *Nature Genet.* In press v. 45 (2013); Northcott, P. A. et al. *Nature Rev. Cancer* 12, 818-834 (2012). The in vivo observations are reinforced by the requirement of BAF for Topo2A binding at DNase-I-hypersensitive BRG1 binding sites (FIG. 3B-E).

The dependence of Topo2A on BAF function offers a possible explanation for the frequency with which BAF subunit mutations are detected in screens for driving mutations in human cancers. Anaphase bridges are often forcibly severed during cytokinesis (Janssen, A., van der Burg, M., Szuhai, K., Kops, G. J. & Medema, R. H. *Science* 333, 1895-1898 (2011)), resulting in partial or complete chromosome gains or losses as well as polyploidy if the cell fails to undergo mitosis (Carpenter, A. J. & Porter, A. C. *Mol. Biol. Cell* 15, 5700-5711 (2004); Johnson, M., Phua, H. H., Bennett, S. C., Spence, J. M. & Farr, C. J. *Nucleic Acids Res.* 37, e98 (2009)). At present, the number of BRG1 mutant medulloblastomas analysed for ploidy status is insufficient to determine whether BRG1 mutation results in aneuploidy in human tumors. In the case of medulloblastoma, mutations in BRG1 are often accompanied by activating mutations in the WNT signaling pathways and/or MYC amplification. Northcott, P. A. et al. *Nature Rev. Cancer* 12, 818-834 (2012). Further studies highlighting these pairings will help define the contribution of reduced Topo2A function as a result of BRG1 mutation to tumorigenesis. More recently data from the c-Bio portal has been analyzed to determine if human cancers with BAF subunit mutations have a specific mutational signature. It was found that in each tumor and with each subunit the rates of background mutation are increased or the same as tumors of the same type lacking BAF subunit mutations. These data are consistent with a role of BAF complexes in controlling the binding of Topo2a to chromatin and subsequent untangling DNA at mitosis.

Methods

Brg1 deletion from Brg1$^{fl/fl}$ creER ESCs and MEFs was performed as previously described. Ho, L. et al. *Nature Cell Biol.* 13, 903-913 (2011). Lentiviruses were produced in HEK293T cells using PEI transfection. Cells were synchronized using double thymidine block. Cell cycle analysis was performed according to manufacturer instructions (BD Biosciences). Topo2A ChIP-seq was performed following etoposide fixation. Sano, K., Miyaji-Yamaguchi, M., Tsutsui, K. M. & Tsutsui, K. *PLoS ONE* 3, e4103 (2008). qPCR, immunofluorescence, immunoprecipitation and western blotting were done using standard protocols. The chromatin fraction from nuclei in varying concentrations of NaCl was analysed by western blot.

Immunofluorescence

To quantify anaphase bridges, cells were fixed with 4% paraformaldehyde for 20 min, washed and stained with 4′,6-diamidino-2-phenylindole (DAPI; Sigma). The number of anaphases/telophases with bridges over the total number of anaphases (between 56-187 total anaphases per 25-mm slide) was recorded from each slide for more than four independent experiments. Brg1$^{fl/fl}$ and Brg1$^{fl/fl}$(ERD) ESCs were visualized with DAPI 72 h after tamoxifen treatment. Wild-type MEFs were infected with lentiviruses containing short hairpin RNA (shRNA) to Brg1, BAF250a or Top2a and analysed 48-96 h after infection.

To stain for Topo2A and centromeres/microtubules, cells were blocked with 5% BSA/1% goat serum in phosphate buffered saline with 0.1% Tween-20 (PBST) for 1 h following fixation and incubated with anti-centromere (Antibodies Inc.) or anti-g-tubulin (Sigma) and anti-Topo2A (Santa Cruz) for 2 h. After several washes, anti-human Alexa Fluor 488 and anti-rabbit Alexa Fluor 568 were added for 1 h. The cells were then stained with DAPI for 10 min and washed 3×PBS for 10 min each. The coverslips were mounted on slides with Vectashield Hard Mount (Vector Labs).

To quantify anaphase bridges from paraffin-embedded human tumor samples, slides were incubated 2×25 min in xylenes, then rehydrated in 100% ethanol, then 95% ethanol, then water, for 2 min each. The slides were boiled in citrate buffer (pH 6.0) (Vector Labs) for 20 min and washed 2×5 min in PBS-Tween. The slides were then stained with DAPI for 10 min and washed 3×5 min with PBS before mounting with Vectashield Hard Mount.

Cell Synchronization

ESCs were incubated with 2 mM thymidine for 7-8 h, released into fresh media for 7 h, and then incubated with thymidine again for 7 h. The cells were washed several times with PBS, released into fresh media, and collected at time points thereafter.

Cell Cycle Analysis

The cell cycle analysis was performed using BD Biosciences BrdU-FITC FACS kit. ESCs were incubated with BrdU for 1 h and MEFs were incubated with BrdU for 4 h. Brg1$^{fl/fl}$ and Brg1$^{fl/fl}$(ERD) ESCs were analysed 72 h after tamoxifen treatment. Caffeine was added to media 2 h before BrdU incubation. To determine the percent of cells in G2/M, DNA was stained with 7-AAD and analysed by FACS.

H3(S10)P Cell Cycle Analysis

Brg1$^{fl/fl}$ ESCs were infected with interference-RNA-resistant wild-type human Topo2A or Topo2A(S1524A) and shRNAs to mouse Top2a. Cells were stained with anti-H3(S10)P and analysed by flow cytometry 72 h after treatment with or without tamoxifen.

Metaphase Spread Preparation

MEFs were grown to 85% confluence and incubated for 4 h with colcemid. Cells were collected and swelled by drop-wise addition of 1:1 0.4% KCl/0.4% sodium citrate for 7 min at 37° C. Cells were then fixed by dropwise addition of 3:1 methanol/acetic acid for 20 min, spun down and fixed for another 30 min. Metaphases were dropped onto slides, dried on wet paper towels and stained with DAPI for visualization. Chromosomes were then measured and counted using ImageJ software. To analyse polyloidy, only cells with greater than 35 chromosomes were counted to eliminate artifacts due to partial spreads.

Gene Expression Profiling and Analysis

RNA was isolated using TRIzol (Invitrogen) and reverse transcribed into complementary DNA using SuperScript III reverse transcriptase (Invitrogen). qPCR was performed on the StepOnePlus (ABI) machine using FastStart Universal SYBR Green Master with ROX (Roche).

Immunoprecipitation

Nuclei were isolated from cells with buffer A (25 mM HEPES, pH 7.6, 5 mM MgCl$_2$, 25 mM KCl, 0.05 mM EDTA, 10% glycerol, 0.1% NP-40) and lysed for 30 min in immunoprecipitation buffer (50 mM Tris-HCl, pH 8.0, 150 mM NaCl, 0.1% NP-40). The chromatin was removed using centrifugation and the lysates were pre-cleared with 20 ml Protein A or Protein G Dynabeads for 30 min. The protein concentration was quantitated using the bicinchoninic acid (BCA) assay (Pierce) and adjusted to a final volume of 200 ml at a final concentration of 1.5 mg ml$^{-1}$ with immunoprecipitation buffer. Each immunoprecipitate was incubated with 3 mg of anti-BRG1 (Santa Cruz), anti-Topo2A (Abcam), anti-BAF45d (Crabtree laboratory), anti-BAF47 (Santa Cruz), anti-BAF57 (Bethyl), anti-BAF155 (Crabtree laboratory), anti-BAF60a (BD Transduction Laboratories), anti-BAF250a (Santa Cruz), anti-BAF180 (Bethyl), anti-BAF250b (Santa Cruz, Bethyl), anti-SS18 (Santa Cruz) anti-BAF200 (Santa Cruz) or anti-IgG (Santa Cruz) overnight at 4° C. and then for 2 h with 20 ml Protein A/G Dynabeads. The beads were washed four times with 1 ml immunoprecipitate buffer and re-suspended in 10 ml gel loading buffer (4× lithium dodecyl sulfate buffer; Invitrogen).

Glycerol Gradient Centrifugation Analysis

ESCs were lysed in buffer A (10 mM HEPES, pH 7.6), 25 mM KCl, 1 mM EDTA, 10% glycerol, 1 mM DTT and protease inhibitors (complete mini tablets (Roche) supplemented with 1 mM phenylmethylsulphonyl fluoride) on ice. Nuclei were sedimented by centrifugation (1,000 g), re-suspended in buffer C (10 mM HEPES, pH 7.6), 3 mM MgCl$_2$, 100 mM KCl, 0.1 mM EDTA, 10% glycerol, 1 mM dithiothreitol (DTT) and protease inhibitors), and lysed by the addition of ammonium sulphate to a final concentration of 0.3 M. Soluble nuclear proteins were separated by insoluble chromatin fraction by ultracentrifugation (100,000 g) and precipitated with 0.3 mg ml$^{-1}$ ammonium sulphate for 20 min on ice. Protein precipitate was isolated by ultracentrifugation (100,000 g) and re-suspended in HEMG-0 buffer (25 mM HEPES, pH 7.9, 0.1 mM EDTA, 12.5 mM MgCl$_2$, 100 mM KCl) for glycerol gradient analyses. 800 mg of protein was overlaid on to a 10-ml 10-30% glycerol (in HEMG buffer) gradient prepared in a 14×89 mm polyallomer centrifuge tube (Beckman). Tubes were placed in a SW-40 swing bucket rotor and centrifuged at 4° C. for 16 h at 40,000 r.p.m. 0.5-ml fractions were collected and used in gel electrophoresis and subsequent western blotting analyses.

Western Blots

Nuclei were isolated from cells with buffer A (25 mM HEPES, pH 7.6, 5 mM MgCl$_2$, 25 mM KCl, 0.05 mM EDTA, 10% glycerol, 0.1% NP-40) and lysed for 30 min in RIPA buffer (10 mM Tris, pH 7.4, 150 mM NaCl, 0.1% SDS, 0.5% sodium deoxycholate, 1% Triton X-100, 1 mM EDTA). Chromatin was either spun out or samples were sonicated before BCA analysis. Equal amounts of protein were boiled in gel loading buffer and loaded onto 4-10% BisTris NuPage gels. After transfer, blots were blocked in 5% BSA and incubated with anti-BRG1, anti-Topo2A, anti-phosphotyrosine (Millipore), anti-phosphoserine (Millipore) or anti-ubiquitin (Santa Cruz). Proteins were detected using the LI-COR detection system or enhanced chemiluminescence (ECL)/autoradiography for SUMO-Topo2A.

Chromatin Association Assay

Nuclei were isolated using buffer A and re-suspended in 20 mM Tris-HCl, pH 7.6, 3 mM EDTA at 60 million cells per ml. Samples of 25 ml were alloquotted into tubes and NaCl concentrations were adjusted to a final volume of 50 ml. Samples were gently mixed and incubated on ice for 20 min and centrifuged at high speed for 20 min to isolate chromatin. The lysate was removed and the chromatin pellet was re-suspended in 120 ml gel loading dye. The pellet was solubilized using sonication and the association of Topo2A to chromatin was analysed using western blotting.

ATPase Assay

ATPase assay was adapted from the literature. Bultman, S. J., Gebuhr, T. C. & Magnuson, T. A. *Genes Dev.* 19, 2849-2861 (2005). Immunoprecipitations were performed as described above with anti-BRG1 antibody. Immunoprecipitates were washed a final time with 10 mM Tris-HCl, pH 7.5, 50 mM NaCl, 5 mM MgCl$_2$, 1 mM DTT and re-suspended in 20 ml assay buffer (10 mM Tris-HCl, pH 7.5, 50 mM NaCl, 5 mM MgCl$_2$, 20% glycerol, 1 mg ml$^{-1}$ BSA, 0.5 mM ATP, 20 nM plasmid DNA, 50 µCi ml$^{-1}$ g-$^{32}$P ATP, 1 mM DTT, protease inhibitors). The reaction was agitated at 37° C. for 1 h (or when approximately 50% of ATP was converted to inorganic phosphate). Reaction mixture (0.5 ml) was spotted onto PEI cellulose plates and thin layer chromatography was performed in 0.5 M LiCl and 1 M formic acid. The plates were dried and imaged using phosphorimaging. The enzymatic activity was quantitated as a ratio of product ($^{32}$P-P$_i$) to starting material (g-$^{32}$P ATP). Values were normalized to the activity of wild-type BRG1 (100%) and vector control (0%) cells.

Chromatin Immunoprecipitation

For the BRG1 ChIP, 40 million ESCs were fixed for 12 min in 1% formaldehyde at room temperature (25° C.). Nuclei were sonicated in 1 ml ChIP lysis buffer (50 mM HEPES, pH 7.5, 150 mM NaCl, 2 mM EDTA, 1% Triton X-100, 0.1% SDS) to yield fragments between 200-500 base pairs. 500 ml of lysate was incubated with 5 mg of anti-BRG1 (Crabtree laboratory) or 5 mg anti-rabbit IgG and rotated overnight at 4° C. and then for 2 h with 20 ml Protein A/G Dynabeads. After five washes with ChIP lysis buffer and one wash in 10 mM Tris-HCl, pH 8.0, 1 mM EDTA (TE), DNA was eluted by boiling in 10% Chelex slurry.

The etoposide ChIP of Topo2A was adapted from the literature. Sano, K., Miyaji-Yamaguchi, M., Tsutsui, K. M. & Tsutsui, K. *PLoS ONE* 3, e4103 (2008). Specifically, 20 million ESCs were treated with 100 mM etoposide for 10 min. Cells were washed once with PBS and lysed with 1 ml of a buffer containing 1% Sarkosyl, 10 mM Tris-HCl, pH 7.5, 10 mM EDTA and protease inhibitor. A solution of 7 M CsCl (7 M) was added to a final concentration of 0.5 M and the lysate was sonicated to yield fragments between 200-500 base pairs. ChIP buffer (300 ml) was added to 300 ml of lysate for a final concentration of 50 mM HEPES, pH 7.5, 300 mM NaCl, 1 mM EDTA, 1% Triton X-100, 0.1% DOC, and 0.1% SDS and 3 mg anti-Topo2A pre-bound to 20 ml Protein G Dynabeads was added. The lysate was rotated overnight at 4° C. and washed four times with ChIP lysis buffer, one time with LiCl buffer (10 mM Tris, pH 8.0, 0.25 M LiCl, 0.5% NP-40, 0.5% DOC, 1 mM EDTA) and one time with TE. The DNA was eluted with 300 ml of 1% SDS, 0.1 M NaHCO$_3$ for 20 min and removed from the beads. The solution was adjusted to 200 mM NaCl, 10 mM EDTA, 40 mM Tris, pH 6.5, and 0.2 mg ml$^{-1}$ RNase A was added for 30 min at 37° C. Proteinase K was added to 0.03 mg ml$^{-1}$ and digested overnight at 55° C. The DNA was extracted with phenol/chloroform and precipitated with ethanol for analysis by qPCR.

ChIP-Seq and Analysis

The library preparation and sequencing was performed as previously described. Barski, A. et al. *Cell* 129, 823-837 (2007). Raw ChIP-seq reads were mapped to the *Mus musculus* genome (build mm9/NCBI37) using the short-read aligner Bowtie (version 0.12.7). Langmead, B., Trapnell, C., Pop, M. & Salzberg, S. L. *Genome Biol.* 10, R25 (2009).

Peaks were then called using Model-base analysis of ChIP-seq (MACS) (version 1.4.1). Zhang, Y. et al. *Genome Biol.* 9, R137 (2008). Further analysis was aided by the Bedtools suite (version 2.16.2). Quinlan, A. R. & Hall, I. M. *Bioinformatics* 26, 841-842 (2010). Genome annotations were acquired from the UCSC Genome Browser (http://genome.ucsc.edu/). Kent, W. J. et al. *Genome Res.* 12, 996-1006 (2002); Meyer, L. R. et al. *Nucleic Acids Res.* 41, D64-D69 (2012).

Topoisomerase Activity Assay

Reactions contain: 150 ng kinetoplast DNA (Topogen), 50 mM Tris-HCl, pH 8.0, 150 mM NaCl, 10 mM MgCl$_2$, 2 mM ATP, a standard Topo2A immunoprecipitate or varying amounts of recombinant Topo2A (Topogen).

Lentiviral Infection

HEK293T cells were transfected with lentiviruses containing vector alone, wild-type BRG1, BRG1 point mutants, wild-type human Topo2A or human Topo2A(S1524A), or with vectors containing shRNA to Brg1, (Clone ID TRCN0000071386), Arid1a (Clone ID TRCN0000071395, Origene) or Top2a (Clone ID V2LMM_11295). 48 h later, supernatants were collected and centrifuged at 20,000 r.p.m. for 2 h. Viral pellets were re-suspended in PBS and used to infect ESCs in suspension or MEFs by spinfection. Cells were selected with puromycin and collected 48-96 h after infection for analysis.

Example 2

Synthetic Lethal Screen Comparing ARID1A Wild-Type and ARID1A Mutant Cell Lines

Figure 11A:
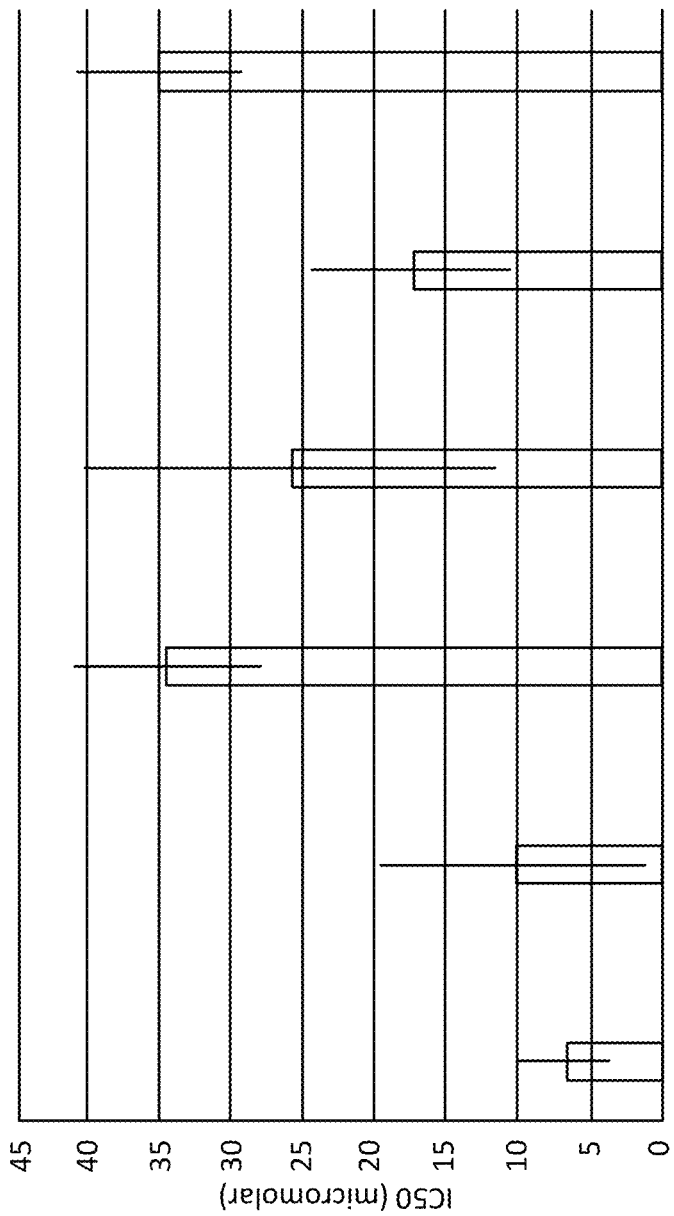
FIG. 11A-FIG. 11C. Synthetic lethal screen comparing the sensitivity of ARID1A wild-type cells (293T and ES2) and ARID1A mutant cells (Hec1b, SKOV3, T47D, and TOV21G) to treatment with topoisomerase inhibitors. Values of IC50 (µM) are plotted on the y-axis, with error bars as shown.
Figure 11B:
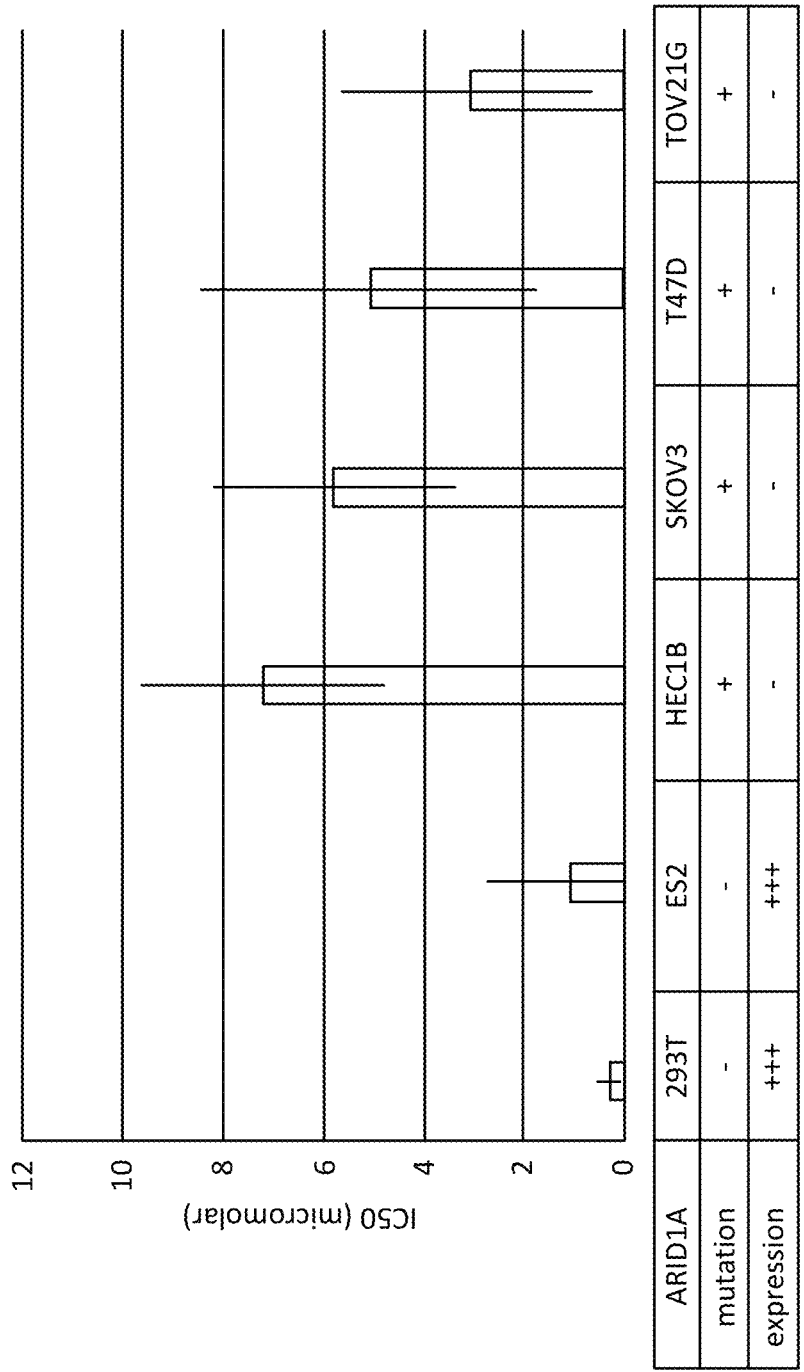
Figure 11C:
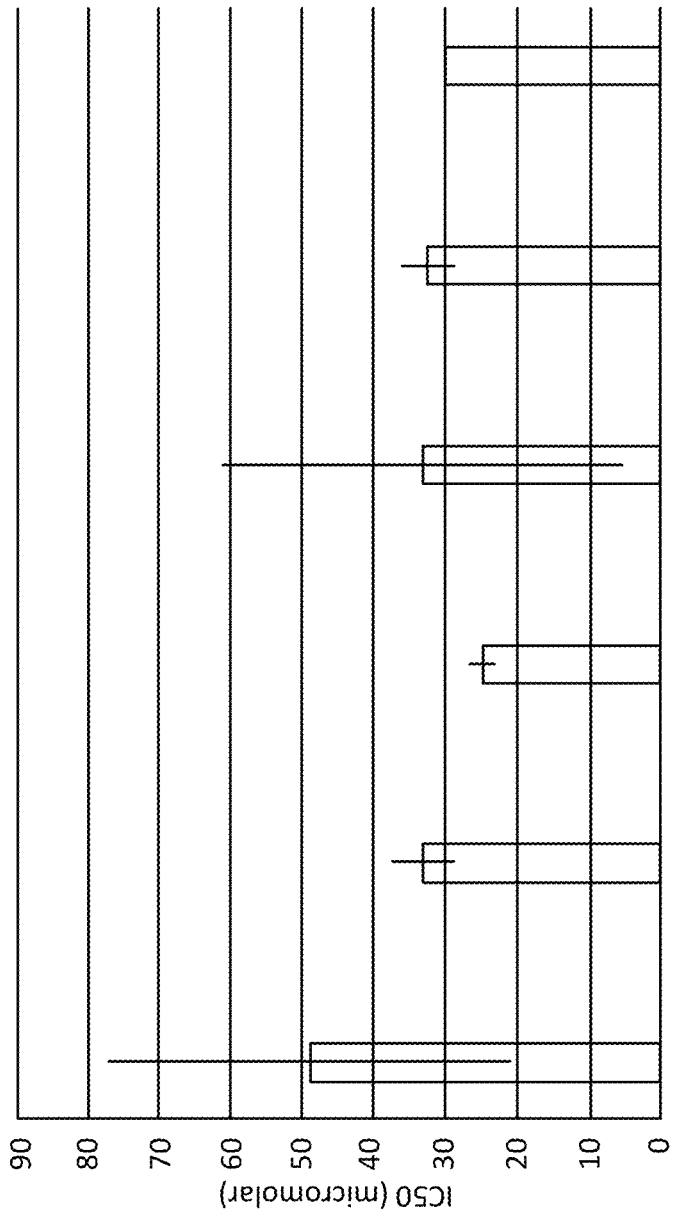

FIG. 11A-FIG. 11C shows a comparison of the sensitivity of various cell lines to treatment with various topoisomerase inhibitors (panel A, etoposide; panel B, doxorubicin; panel C, ICRF-193). The cell lines correspond to wild type cells (293T and ES2) and ARID1A mutant cells (Hec1b, SKOV3 e, T47D, and TOV21G) that do not have protein expression of ARID1A. In each case, 1500-2000 cells were plated in 100 ul per 384 well clear bottom black plate (E&K Scientific EK-30091). After 24 hours, doses of the listed compound diluted in DMSO were pinned into the plates. After 48 hours, 10 ul of Cell Titer Blue (Promega) was added, and the cells were placed back in the incubator. Fluorescence was read after another 24 hours. IC50 values (µM) are reported on the y-axis.

Example 3

Figure 12A:
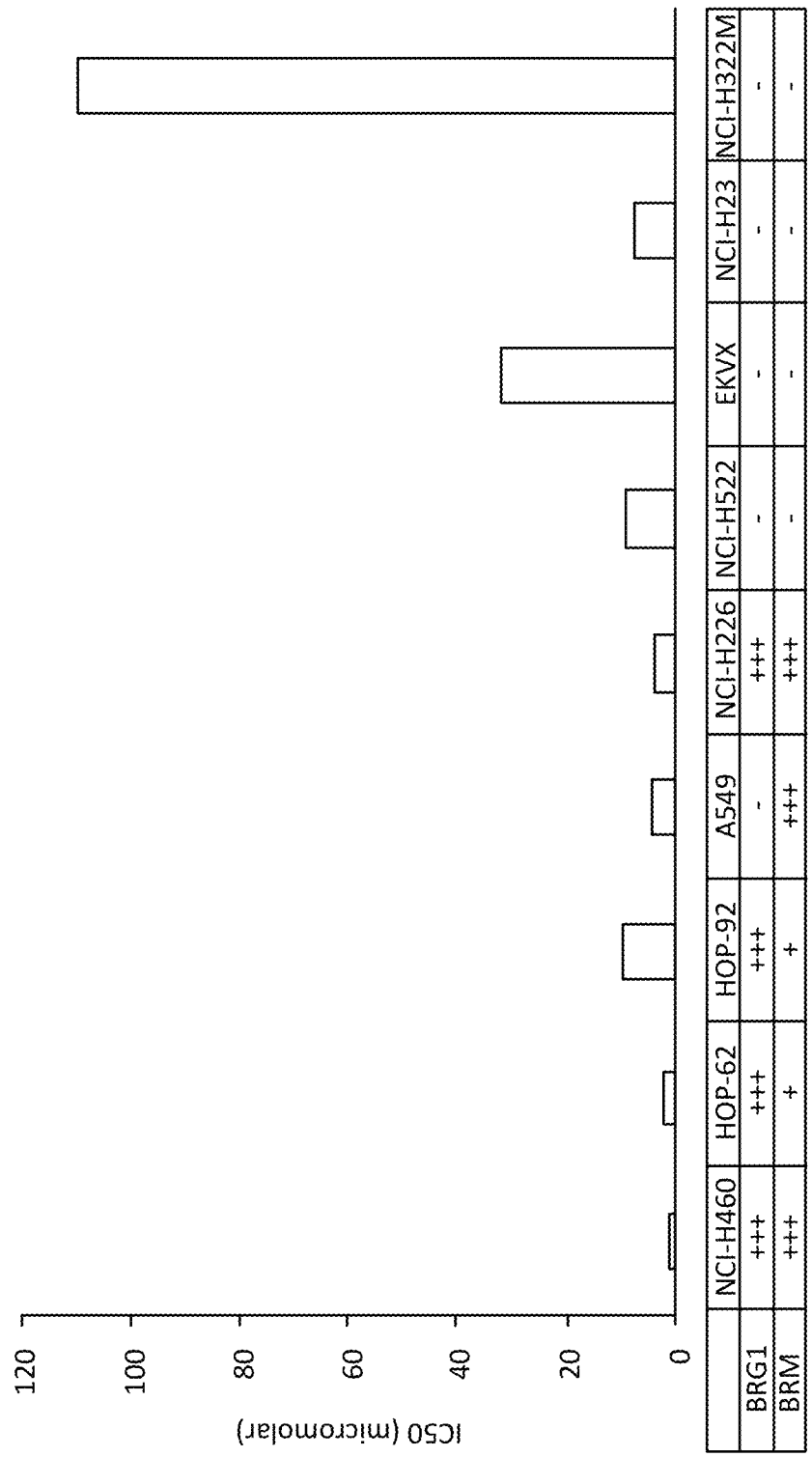
FIG. 12A and FIG. 12B. Comparison of the sensitivity of NCI-60 cancer cell lines to topoisomerase inhibitors using data obtained from CellMiner™ database. Note that cells with mutations in subunits of the BAF complex are more resistant to topoisomerase inhibitors. Without intending to be bound by theory, this observation is consistent with the observation that BAF complex function is necessary for the binding of Topo2a to DNA. Thus in a cancer cell having compromised BAF function Topo2a will not bind to DNA and inhibiting Topo2a will therefore not lead to the death of the cancer cell.
Figure 12B:
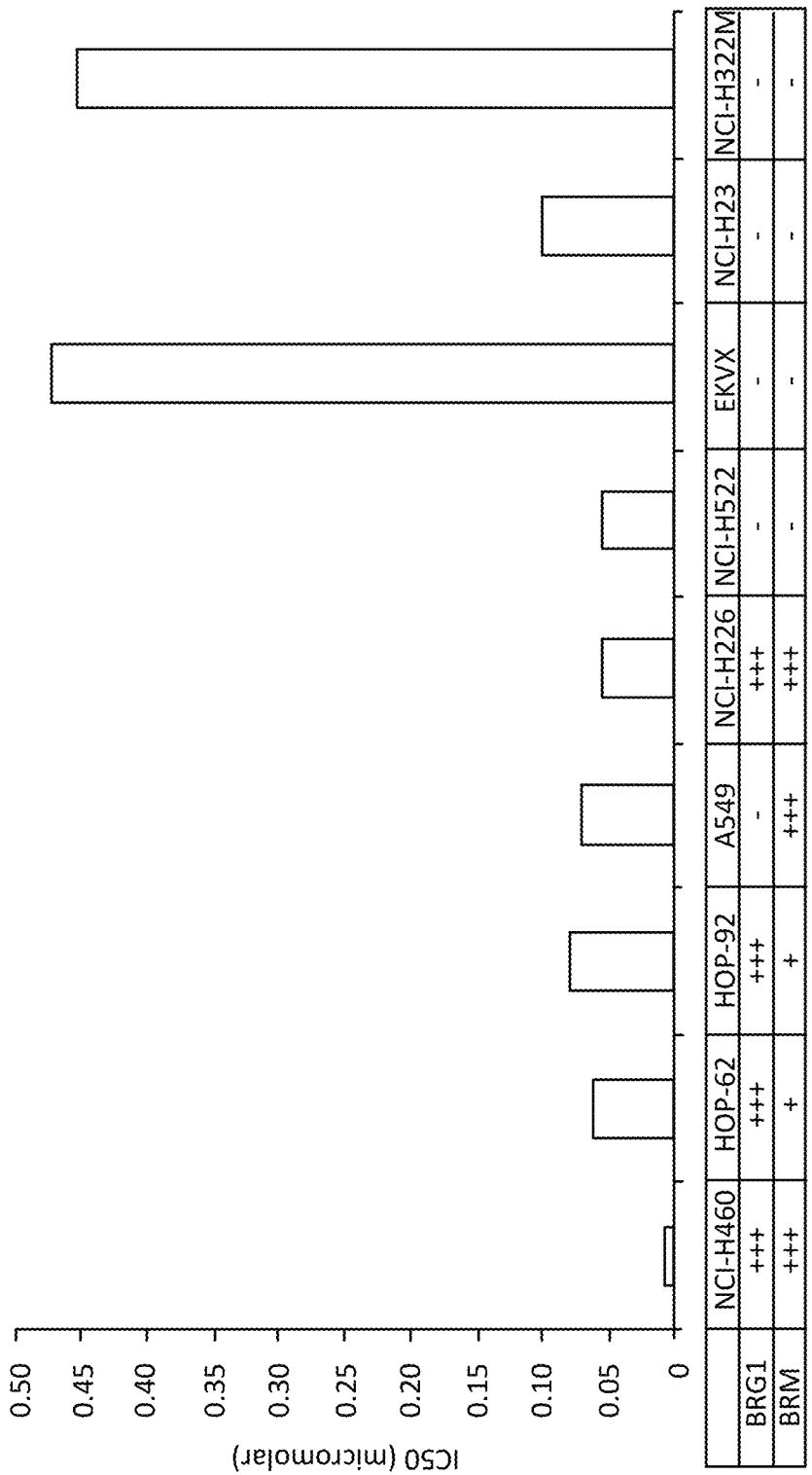

Data Mining to Determine Sensitivity of NCI60 Cell Lines to Topoisomerase Inhibitors FIGS. 12A and 12B show the sensitivity of various NCI60 cell lines to etoposide and doxorubicin, respectively. Data were obtained by mining an existing database. See CellMiner: a relational database and query tool for the NCI-60 cancer cell lines, Shankavaram et al. BMC Genomics (2009) 10:277; doi:10.1186/1471-2164-10-277. Cell lines NCI-H460, HOP-62, HOP-92, A549, and NCI-H226 are non small cell lung cancer lines that express either BRG1, BRM or both, while NCI-H522, EKVX, NCI-H23, and NCI-H322M are deficient in both BRG1 and BRM expression. IC50 values (µM) are reported on the y-axis.

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. A method for treating cancer in a patient having been identified as having a decreased activity of at least one BAF subunit in a tumor cell of the patient, the method comprising:
    administering to the patient an effective amount of a topoisomerase inhibitor that does not cause double-stranded breaks in genomic DNA,
    wherein the at least one BAF subunit is encoded by ARID1A, and
    wherein the topoisomerase inhibitor that does not cause double-stranded breaks in genomic DNA is aurintricarboxylic acid, HU-331, epigallocatechin gallate, genistein, quercetin, or ICRF-193.

2. The method of claim 1, wherein the cancer is a colorectal cancer, a clear-cell ovarian cancer, a serous ovarian cancer, a pancreatic cancer, a gastric cancer, a bladder cancer, a hepatocellular cancer, a renal cancer, a squamous cell carcinoma, a breast cancer, a medulloblastoma, a glioma, a melanoma, a lung cancer, a prostate cancer, a sarcoma, a malignant rhabdoid tumor, or a hematologic malignancy.

3. The method of claim 2, wherein the cancer is a colorectal cancer, a clear-cell ovarian cancer, a pancreatic cancer, a gastric cancer, a bladder cancer, a hepatocellular cancer, a renal cancer, a breast cancer, a medulloblastoma, a lung cancer, a prostate cancer, a sarcoma, a malignant rhabdoid tumor, or a hematologic malignancy.

4. The method of claim 1, wherein the patient is identified by sequencing a portion of a gene encoding the at least one BAF subunit in a tumor sample and in a non-tumor sample from the patient, and wherein a mutation in the gene encoding the at least one BAF subunit in the tumor sample compared to the non-tumor sample indicates the decreased activity of the at least one BAF subunit in the tumor sample.

5. The method of claim 1, wherein the patient is identified by measuring transcription of a gene encoding the at least one BAF subunit in a tumor sample and in a non-tumor sample from the patient, and wherein a decreased transcription of the gene encoding the at least one BAF subunit in the tumor sample compared to the non-tumor sample indicates the decreased activity of the at least one BAF subunit in the tumor sample.

6. The method of claim 1, wherein the patient is identified by measuring protein expression of the at least one BAF subunit in a tumor sample and in a non-tumor sample from the patient, and wherein a decreased protein expression of the at least one BAF subunit in the tumor sample compared to the non-tumor sample indicates the decreased activity of the at least one BAF subunit in the tumor sample.

7. The method of claim 1, wherein the patient is identified by measuring post-translational modification of the at least one BAF subunit in a tumor sample and in a non-tumor sample from the patient, and wherein an altered post-translational modification of the at least one BAF subunit in the tumor sample compared to the non-tumor sample indicates the decreased activity of the at least one BAF subunit in the tumor sample.

8. The method of claim 1, wherein the patient is identified by measuring decatenation of DNA by topoisomerase IIa in a tumor sample and in a non-tumor sample from the patient, and wherein a decreased decatenation of DNA by topoisomerase IIa in the tumor sample compared to the non-tumor sample indicates the decreased activity of the at least one BAF subunit in the tumor sample.

9. The method of claim 1, wherein the patient is identified by determining activities of at least two BAF subunits in a tumor sample and in a non-tumor sample from the patient.

10. The method of claim 1, wherein the patient is identified by determining activities of at least five BAF subunits in a tumor sample and in a non-tumor sample from the patient.

11. The method of claim 1, wherein the patient is identified by sequencing a portion of a gene encoding the at least one BAF subunit, by measuring transcription of a gene encoding the at least one BAF subunit, by measuring protein expression of the at least one BAF subunit, by measuring post-translational modification of the at least one BAF subunit, or by measuring decatenation of DNA by topoisomerase IIa in a tumor sample and in a non-tumor sample from the patient.

* * * * *